(12) United States Patent
Vilen et al.

(10) Patent No.: US 8,795,653 B2
(45) Date of Patent: Aug. 5, 2014

(54) METHODS FOR REPRESSING B CELL AUTOANTIBODY SECRETION AND FOR TREATING AUTOIMMUNE DISORDERS BY ADMINISTRATION OF HEMATOPOIETIC STEM CELLS AND MACROPHAGE-COLONY STIMULATING FACTOR

(75) Inventors: Barbara J. Vilen, Durham, NC (US); Michelle Kilmon, Morrisville, NC (US); Jennifer A. Rutan, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1198 days.

(21) Appl. No.: 11/376,375

(22) Filed: Mar. 15, 2006

(65) Prior Publication Data

US 2006/0188473 A1  Aug. 24, 2006

Related U.S. Application Data

(63) Continuation-in-part of application No. PCT/US2004/030325, filed on Sep. 16, 2004.

(60) Provisional application No. 60/503,534, filed on Sep. 16, 2003.

(51) Int. Cl.
*A01N 63/00* (2006.01)
*A61K 45/00* (2006.01)
*A61K 47/00* (2006.01)

(52) U.S. Cl.
USPC ................................ 424/93.71; 424/278.1

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 5,716,827 A | 2/1998 | Tsukamoto et al. | |
| 5,750,397 A | 5/1998 | Tsukamoto et al. | |
| 5,763,197 A | 6/1998 | Tsukamoto et al. | |
| 5,914,108 A | 6/1999 | Tsukamoto et al. | |
| 6,015,554 A | 1/2000 | Galy | |
| 6,093,872 A | 7/2000 | Kaneshima et al. | |
| 6,503,509 B1 | 1/2003 | Vilen et al. | |
| 2002/0085993 A1 | 7/2002 | Steinman et al. | |
| 2002/0090381 A1 | 7/2002 | Bottomly et al. | |
| 2002/0114793 A1 | 8/2002 | Edelson et al. | |
| 2002/0141977 A1 | 10/2002 | Collins et al. | |
| 2002/0146396 A1 | 10/2002 | Albert et al. | |
| 2003/0035790 A1 | 2/2003 | Chen et al. | |
| 2003/0077284 A1 | 4/2003 | Vilen et al. | |
| 2003/0091548 A1 | 5/2003 | Fathman | |
| 2003/0095957 A1 | 5/2003 | Crystal et al. | |
| 2003/0133913 A1 | 7/2003 | Tomai et al. | |
| 2003/0133914 A1 | 7/2003 | Edelson et al. | |
| 2004/0009949 A1 | 1/2004 | Krieg | |
| 2005/0221482 A1 | 10/2005 | Burt et al. | |

OTHER PUBLICATIONS

Burt, R.K., et al. Blood, 1998;92(10):3505-3514.*
Weisdorf, D.J., et al. Blood, 1995;85(12):3452-3456.*
Kilmon, M.A., et al. J. Immunol., 2005;175:37-41.*
Paul, W.E., editor. Fundamental Immunology, 1999, pp. 1517-1519 and 1216-1219.*
Masaoka, T., et al. Brit. J. Haematol. 1990;76:501-505.*
Jones, O.Y., et al. J. Immunol. 2004;172:5415-5419.*
Bulman, P.M. and G. Hunder, Ann. Int. Med. 1998;129(12):1095-1096.*
Cooke, K.R., et al. J. Clin. Invest.2001;107(12):1581-1589.*
Burt et al. "Nonmyeloblative Hematopoietic Stem Cell Transplantation for Systemic Lupus Erythematosus" *JAMA* 295(5):527-535 (2006).
Carroll, Michael "Innate immunity in the etiopathology of autoimmunity" *Nature Immunology* 2(12):1089-1090 (2001).
Culton et al. "Early Preplasma Cells Define a Tolerance Checkpoint for Autoreactive B Cells" *The Journal of Immunology* 176(2):790-802 (2006).
Doxsee et al. "The Immune Response Modifier and Toll-Like Receptor 7 Agonist S-27609 Selectively Induces IL-12 and TNF-• Production in DC11c+CD11b+CD8 Dendritic Cells" *The Journal of Immunology* 171:1156-1163 (2003).
Goodnow, Christopher "Balancing Immunity and tolerance: Deleting and tuning lymphocyte repertoires" *Proc. Natl. Acad. Sci. USA* 93(6):2264-2271 (1996).
Herrmann et al. "Etiopathogenesis of systemic lupus erythematosus" *Trends—Immunology Today* 21(9):424-426 (2000).
Homann et al. "CD40L Blockade Prevents Autoimmune Diabetes by Induction of Bitypic NK/DC Regulatory Cells" *Immunity* 16(3):403-415 (2002).
Jayne et al. "Autologous stem cell transplantation for systemic lupus erythematosus" *Lupus* 13:168-176 (2004).
Kilmon et al. "B cell tolerance to Sm is mediated by dendritic cells and macrophages" Poster Abstract, Steamboat Springs, CO (2004).

(Continued)

*Primary Examiner* — Gerald R Ewoldt
(74) *Attorney, Agent, or Firm* — Myers Bigel Sibley & Sajovec

(57) ABSTRACT

The invention provides isolated regulatory immune cells as well as cell cultures and conditioned media derived therefrom. Also provided are methods of repressing B cell autoantibody production and/or secretion and methods of treating autoimmune disorders using regulatory immune cells or precursors thereto such as hematopoietic stem cells (HSC). The invention also provides methods of repressing B cell autoantibody production and/or secretion and methods of treating autoimmune disorders by administration of HSC and Macrophage-Colony Stimulating Factor (M-CSF). Further provided are methods of diagnosing in a mammalian subject a defect in regulatory cell mediated repression of autoantibody secretion by B cells.

25 Claims, 20 Drawing Sheets

(56) References Cited

OTHER PUBLICATIONS

Kilmon et al. "Cutting Edge: Low-Affinity, Smith Antigen-Specific B Cells Are Tolerized by Dendritic Cells and Macrophages" *The Journal of Immunology* 175(1):37-41 (2005).

Kim et al. "Independent Trafficking of Ig-•/Ig-• and •-Heavy Chain Is Facilitated by Dissociation of the B Cell Antigen Receptor Complex" *The Journal of Immunology* 175(1):147-154 (2005).

Krueger et al. "Autoantigen-specific protection of non-obese diabetic mice from cyclophosphamide-accelerated diabetes by vaccination with dendritic cells" *Diabetologia* 46:1357-1365 (2003).

Levite et al. "Beneficial Effects of Bone Marrow Transplantation on the Serological Manifestations and Kidney Pathology of Experimental Systemic Lupus Erythematosus" *Cellular Immunology* 162(1):138-145 (1995).

Marmont, Alberto "Stem cell transplantation for severe autoimmune diseases: progress and problems" *Haematologica* 83:733-743 (1998).

Marmont et al. "Long term complete remission of severe nephrotic syndrome secondary to diffuse global (IV-G) lupus nephritis following autologous, haematopoietic peripheral stem (CD34$^+$) cell transplantation" *Lupus* 15:44-46 (2006).

Mellor et a. "Cutting Edge: Induced Indoleamine 2,3 Dioxygenase Expression in Dendritic Cell Subsets Suppresses T Cell Clonal Expansion" *The Journal of Immunology* 171:1652-1655 (2003).

Meloni et al. "Blast Crisis of Chronic Myelogenous Leukemia in Long-Lasting Systemic Lupus Erythematosus: Regression of Both Diseases After Autologous Bone Marrow Transplantation" *Blood* 89(12):4659-4666 91997).

Nelson et al. "Pre-existing Autoimmune Disease in Patients with Longterm Survival After Allogeneic Bone Transplantation" *The Journal of Rheumatology* 24(supp 48):23-29 (1997).

Pasare et al. "Toll Pathway-Dependent Blockade of CD4$^+$CD25$^+$ T Cell-Mediated Suppression by Dendritic Cells" *Science* 299:1033-1036 (2003).

Sakaguchi, Shimon "Animal models of autoimmunity and their relevance to human diseases" *Current Opin. Immunol.* 12(6):684-690 (2000).

Snowden, Dr. J.A. "Haemopoietic Stem Cell Transplantation for Autoimmune Diseases" 99:9-22 (1997).

Snowden et al. "Prolonged remission of longstanding systemic lupus erythematosus after autologous bone marrow transplant for non-Hodgkin's lymphoma" *Bone Marrow Transplantation* 19:1247-1250 (1997).

Talaulikar et al. "Autologous peripheral blood stem cell transplantation with in vivo T-cell depletion for life threatening refractory systemic lupus erythematosus" *Lupus* 14:159-163 (2005).

Traynor et al. "Hematopoietic Stem Cell Transplantation for Severe and Refractory Lupus" *Arthritis & Rheumatism* 46(11):2917-2923 (2002).

Tyndall et al. "Haematopoietic stem cell transplantation in the treatment of severe autoimmune disease: results from phase I/II studies, prospective randomized trials and future directions" *Clinical and Experimental Immunology* 141:1-9 (2005).

Vilen et al. "Transmodulation of BCR Signaling by Transduction-Incompetent Antigen Receptors: Implications for Impaired Signaling in Anergic B Cells" *The Journal of Immunoloty* 168(9):4344-4351 (2002).

Vilen et al. "Mechanisms of B cell tolerance to Self Antigen" presentation—International Inhibitors Symposium, Chapel Hill, NC 1 pg. (2003).

Vilen, Barbara "Abstract" presentation—Lupus Research Institute, New York, NY 9 pgs. (2003).

Vilen, Barbara "Tolerance to Sm is reversible and mediated by dendritic cells" presentation—University of Virginia, Charlottesville, VA 20 pgs. (2004).

Vilen, Barbara "Abstract" poster presentation—Keystone Symposium, Steamboard Springs, CO 10 pgs. (2004).

Vilen, Barbara "Tolerance to Sm is reversible and mediated by dendritic cells" presentation—Trudeau Institute, Saranac Lake, NY 24 pgs. (2004).

Vilen, Barbara "Dendritic cell and macrophage-mediated tolerance in Systematic Lupus Erythematosus" presentation—Triangle Virology Meeting, Research Triangle Park, NC 23 pgs. (2005).

Nemunaitis et al. "Recombinant Granulocyte-Macrophage Colony-Stimulating Factor After Autologous Bone Marrow Transplantation for Lymphoid-Cancer" The New England Journal of Medicine 324 (25): 1773-1778 (1991).

Adkins et al. "Resolution of Psoriasis After Allogeneic Bone Marrow Transplantation for Chronic Myelogenous Leukemia: Late Complications of Therapy" *Bone Marrow Transplantation* 26:1239-1241 (2000).

Burt et al. "The Promise of Hematopoietic Stem Cell Transplantation for Autoimmune Diseases" *Bone Marrow Transplantation* 31:521-524 (2003).

Khorshid et al. "Nonmyeloablative Stem Cell Transplant in a Patient with Advanced Systemic Sclerosis and Systemic Lupus Erythematosus" *The Journal of Rheumatology* 31(12):2513-2516 (2004).

Marmont. "Immune Ablation with Stem-Cell Rescue: A Possible Cure for Systemic Lupus Erythematosus?" *Lupus* 2:151-156 (1993).

McAllister et al. "Allogeneic Bone Marrow Transplant for Chronic Myelogenous Leukemia in a Patient with Multiple Sclerosis" *Bone Marrow Transplantation* 19:395-397 (1997).

McKendry et al. "Progression of Rheumatoid Arthritis Following Bone Marrow Transplantation" *Arthritis & Rheumatism* 39(7):1246-1253 (1996).

Van Bekkum, "Experimental Basis of Hematopoietic Stem Cell Transplantation for Treatment of Autoimmune Diseases", *Journal of Leukocyte Biology*, 72, pp. 609-620 (2002).

Ikehara et al., "Rationale for Bone Marrow Transplantation in the Treatment of Autoimmune Diseases", *Proc. Natl. Acad. Sci*, 82, pp. 2483-2487, (Apr. 1985).

Wang et al., "Effective Treatment of Autoimmune Disease and Progressive Renal Disease by Mixed Bone-Marrow Transplantation that Establishes a Stable Mixed Chimerism in BXSB Recipient Mice," *Proc. Natl. Acad. Sci*, 96, pp. 3012-3016, (Mar. 1999).

Harley et al., "Genetic Susceptibility to SLE: New Insights from Fine Mapping and Genome-Wide Association Studies", *Nature Reviews / Genetics*, 10, pp. 285-290, (May 2009).

Nath et al., "Genetics of Human Systemic Lupus Erythematosus: the Emerging Picture", *Current Opinion in Immunology*, 16, pp. 794-800, (2004).

Cantor et al., "Systemic Lupus Erythematosus Genome Scan", *Arthritis & Rheumatism*, 50, No. 10, pp. 3203-3210, (Oct. 2004).

\* cited by examiner

METHODS FOR REPRESSING B CELL AUTOANTIBODY SECRETION AND FOR TREATING AUTOIMMUNE DISORDERS BY ADMINISTRATION OF HEMATOPOIETIC STEM CELLS AND MACROPHAGE-COLONY STIMULATING FACTOR

RELATED APPLICATION INFORMATION

This application is a continuation-in-part application of International Application No. PCT/US2004/030325, filed Sep. 16, 2004, which claims the benefit of priority from U.S. Provisional Application Ser. No. 60/503,534, filed Sep. 16, 2003, which applications are incorporated herein by reference in their entireties.

STATEMENT OF FEDERAL SUPPORT

The present invention was made, in part, with the support of grant numbers 5T32AR007416-22 and RO1AI053266 from the National Institutes of Health. The United States government has certain rights to this invention.

FIELD OF THE INVENTION

The present invention relates to immunological cells, compositions and methods; in particular, the present invention relates to cells, compositions and methods for repressing B cell autoantibody secretion and treating and diagnosing autoimmune disease.

BACKGROUND OF THE INVENTION

Systemic lupus erythematosus (SLE) is a multi-organ autoimmune disease characterized by elevated serum autoantibody levels and tissue pathology involving kidney, skin, joints, brain, lung and heart. The predominant autoantigens in SLE are the components of nucleosomes (DNA, histones) and small nuclear ribonucleoprotein particles (Sm, nRNP-A and nRNP-C). The high levels of circulating antibodies induce immune complex deposits in tissues where subsequent complement activation leads to inflammation. Therapies to manage SLE have been limited to drugs that suppress immune function or drugs that control end-organ inflammation.

The mechanisms underlying the breakdown in tolerance associated with SLE remain poorly defined. The presence of polyclonal activators and deficiencies in B cell tolerance mechanisms may both play roles in the production of autoantibodies. Viral infection and microbial agents act as polyclonal B cell activators upon ligation of Toll like receptors (TLRs). Similarly, apoptotic cells have been linked to the autoreactive response of SLE and may also mediate innate immune activation through TLR 9. Binding of polyclonal activators to TLRs may synergize with signals transduced through the BCR to induce B cell activation and differentiation to antibody secreting cells. For example, ligands for TLR2/6, TLR3, TLR4, TLR5, TLR7 and TLR9 have been identified on uncleared apoptotic cells or as products of bacterial or viral infections. Stimulation through these receptors coupled with ligation of antigen-specific BCR may provide sufficient costimulation to drive immune activation.

Several mechanisms that maintain autoreactive B cells in an unresponsive state have been identified using immunoglobulin transgenic mice. The first mechanism induces a functionally inactive state termed anergy. In this model, B cells from hen egg lysozyme-specific immunoglobulin transgenic mice (anti-HEL) develop in the presence of soluble hen egg lysozyme (sHEL). Peripheral B cells from these mice exhibit an unresponsive phenotype characterized by an inability to renew signal transduction upon BCR ligation with self-antigen. These cells exhibit downmodulated surface B cell receptor (BCR), an inability to secrete antibody in response to stimulation with lipopolysaccharide (LPS) and anti-IgM, a shortened half-life and an inability to compete with naïve B cells for follicular niches. Mechanistically, the sustained extracellular response kinase (ERK) activation exhibited by anti-HEL specific B cells acts to inhibit TLR 9-induced plasma cell differentiation.

Another mechanism of tolerance has been described that regulates B cells specific for dsDNA. Immunoglobulin transgenic (IgTg) B cells expressing a BCR specific for dsDNA exhibit a phenotype similar to the anti-HEL B cells. Unlike anti-HEL B cells, anti-dsDNA B cells become activated to secrete autoantibodies upon engagement by activated $T_H$ cells. However, if the T cell help becomes available in the presence of CD4+CD25+ T regulatory ($T_{reg}$) cells, the anti-dsDNA specific B cells fail to develop into autoantibody secreting cells. These data define an indirect role for regulatory T cells in maintaining autospecific B cells in an unresponsive state (Seo and Erickson, (2002) *Immunity* 16:535).

It has previously been reported that B cells specific for lupus-associated Smith antigen (Sm) remain unresponsive by a mechanism involving peripheral anergy. These mice carry a 2-12 immunoglobulin heavy chain transgene paired with a Vk8 light chain transgene encoding a low affinity Sm-specific BCR. 2-12/Vk8 B cells exhibit a mature phenotype, but respond suboptimally to LPS and anti-IgM signaling indicating an anergic phenotype. Unlike the anti-HEL B cells, 2-12/Vk8 cells enter the follicle normally and have a normal life span. In addition, these cells fail to downregulate surface Ig and respond to CD40L and IL-4 suggesting that anergy to Sm can be overcome by T cell co-stimulation.

There is a need in the art for compositions and methods for maintaining and/or rendering autoreactive B cells unresponsive.

SUMMARY OF THE INVENTION

The inventors have discovered that activated regulatory immune cells repress autoantibody (anti-Sm) secretion by B cells. Purification of anergic anti-Sm B cells from the regulatory immune cell population reverses the anergic phenotype allowing the production of autoantibodies upon activation. Mechanistically, it appears that the repressive effect of the regulatory immune cells is through secretion of a soluble factor(s). These findings have important implications for the regulation of B cell autoantibody secretion and the treatment of autoimmune disorder.

According to one aspect, the invention provides a method of repressing B cell autoantibody secretion in a mammalian subject, the method comprising administering a plurality of hematopoietic stem cells (HSC) that can differentiate into dendritic cells (e.g., a myeloid dendritic cell) and/or macrophages to the mammalian subject in an amount effective to repress B cell autoantibody secretion in the mammalian subject.

The invention also provides a method of repressing B cell autoantibody secretion in a mammalian subject, the method comprising: culturing a plurality of HSC under conditions sufficient for the HSC to differentiate into dendritic cells (e.g., myeloid dendritic cells) and/or macrophages; and administering a plurality of the dendritic cells and/or macrophages to the mammalian subject in an amount effective to repress B cell autoantibody secretion in the mammalian subject.

As another aspect, the invention provides a method of treating an autoimmune disorder in a mammalian subject, the method comprising administering HSC that can differentiate into dendritic cells (e.g., myeloid dendritic cells) and/or macrophages to the mammalian subject in an amount effective to treat the autoimmune disorder.

The invention further provides a method of treating an autoimmune disorder in a mammalian subject, the method comprising: culturing a plurality of HSC under conditions sufficient for the HSC to differentiate into dendritic cells (e.g., dendritic cells) and/or macrophages; and administering a plurality of the dendritic cells and/or macrophages to the mammalian subject in an amount effective to treat the autoimmune disorder.

As another aspect, the invention provides an isolated cell selected from the group consisting of:
(a) an isolated dendritic cell (e.g., myeloid dendritic cell), wherein the dendritic cell displays an epitope from a self antigen on the cell surface; and
(b) an isolated macrophage, wherein the macrophage displays an epitope from a self antigen on the cell surface.

As a further aspect, the invention provides an isolated cell selected from the group consisting of:
(a) an isolated dendritic cell (e.g., myeloid dendritic cell), wherein the dendritic cell is activated to secrete a soluble factor that represses B cell autoantibody secretion; and
(b) an isolated macrophage, wherein the macrophage is activated to secrete a soluble factor that represses B cell autoantibody secretion.

As still another aspect, the invention provides a method of repressing B cell autoantibody secretion, the method comprising contacting an autoreactive B cell with:
(a) an isolated regulatory cell of the invention,
(b) a soluble factor comprising IL-6, TNF-$\alpha$, CD40 ligand, or a combination thereof; or
(c) a combination of (a) and (b).

As yet another aspect, the invention provides a method of treating an autoimmune disorder in a mammalian subject, the method comprising administering to the mammalian subject in a treatment-effective amount:
(a) an isolated regulatory cell of the invention;
(b) a soluble factor comprising IL-6, TNF-$\alpha$, CD40 ligand, or a combination thereof; or
(c) a combination of (a) and (b).

As a further aspect, the invention provides a method of activating a cell to produce a soluble factor that represses B cell autoantibody secretion, wherein the cell is a dendritic cell (e.g., myeloid dendritic cell) and/or macrophage, the method comprising contacting the cell with an agent that activates the cell through a Toll Like receptor (TLR), CD40 antigen and/or TNF receptor.

The invention also provides a method of repressing B cell autoantibody secretion in a mammalian subject, the method comprising administering to the mammalian subject an agent that activates dendritic cells (e.g., myeloid dendritic cells) and/or macrophages through TLR, CD40 antigen and/or a TNF receptor in an amount effective to repress autoantibody secretion.

Further provided are methods of treating an autoimmune disorder in a mammalian subject, the methods comprising administering to the mammalian subject an agent that activates dendritic cells (e.g., myeloid dendritic cells) and/or macrophages through a TLR, CD40 antigen and/or a TNF receptor in an amount effective to treat the autoimmune disorder.

The invention also provides a method of repressing B cell autoantibody secretion in a mammalian subject, the method comprising administering to the mammalian subject a soluble factor comprising IL-6, TNF-$\alpha$, CD40 ligand, or a combination thereof in an amount effective to repress B cell autoantibody secretion.

As still a further aspect, the invention provides a method of treating an autoimmune disorder in a mammalian subject, the method comprising administering to the mammalian subject a soluble factor comprising IL-6, TNF-$\alpha$, CD40 ligand, or a combination thereof in an amount effective to treat the autoimmune disorder.

As a further aspect, the invention provides a method of repressing B cell autoantibody secretion in a mammalian subject, the method comprising administering GM-CSF and/or M-CSF to the mammalian subject in an amount effective to repress B cell autoantibody secretion.

Also provided are methods of treating an autoimmune disorder in a mammalian subject, the methods comprising administering GM-CSF and/or M-CSF to the mammalian subject in an amount effective to treat the autoimmune disorder.

The invention further encompasses a method of diagnosing in a mammalian subject a defect in a dendritic cell (e.g., a myeloid dendritic cell) and/or macrophage mediated repression of autoantibody secretion by B cells, the method comprising:
activating a dendritic cell (e.g., myeloid dendritic cell) and/or macrophage from the mammalian subject through a TLR, CD40 antigen and/or a TNF receptor,
detecting the production by the dendritic cell and/or macrophage of a soluble factor comprising IL-6, TNF-$\alpha$, CD40 ligand, or a combination thereof that represses autoantibody secretion by B cells;
wherein a reduction in production of the soluble factor as compared with a control cell indicates a defect in dendritic cell and/or macrophage mediated repression of autoantibody secretion in the mammalian subject.

In particular embodiments, the methods of treating autoimmune disorder further comprise administering to the mammalian subject a treatment effective amount of a B cell depletion therapy.

These and other aspects of the invention are set forth in more detail in the description of the invention below.

DC CM from MRL/lpr mice was untreated (○) or treated with rIL-6 (10 ng/ml) (♦) prior to coculture with B cells from 2-12H/Vκ8 mice (□). Secreted IgM$^a$/κ levels were quantitated by ELISA from day 4 culture supernatant. LPS-stimulated B cells (100%; ▲) secreted 1-10 μg/ml IgM$^a$/κ. *Denotes statistical significance (p=0.0009). Data represent 15 (A), 3 (B) and 3 (C) individual MRL/lpr mice.

Figure 18:
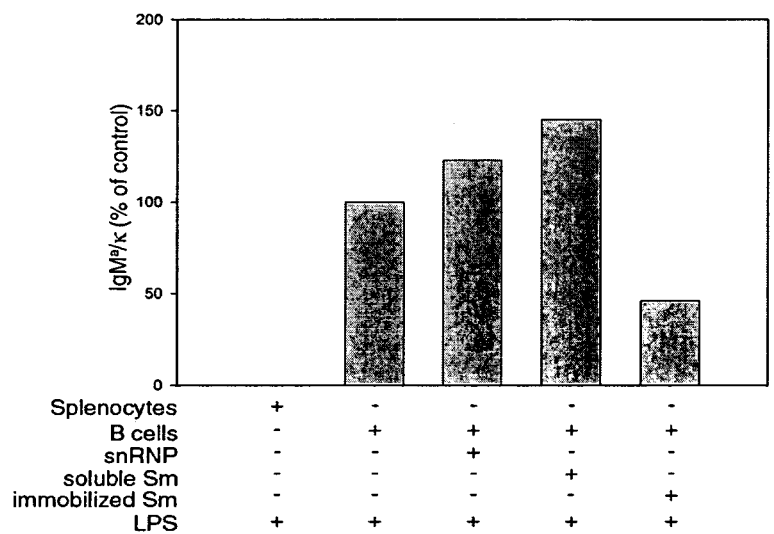

FIG. 18 demonstrates that Sm-specific B cells from 2-12H/Vκ8 mice fail to recognize soluble antigen. Splenic B cells purified by negative selection ($1\times10^5$) were cultured with snRNPs (50 μg/ml), soluble Sm (50 μg/ml) or Sm (50 μg/area) immobilized to plastic. Cultures were treated with LPS (30 μg/ml) and at day 4 the amount of immunoglobulin secretion was quantitated by ELISA.

Figure 19:
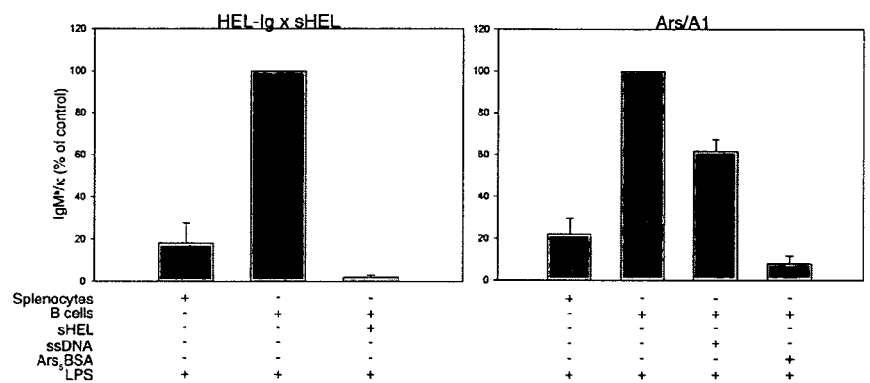

FIG. 19 shows that antigen-mediated tolerance varies in different models. B cells purified from HEL-Ig×sHEL (MD4×ML5) mice were LPS stimulated in the presence or absence of soluble HEL (100 μg/ml) (left panel). Cultures were treated with LPS (30 μg/ml) and at day 4 the amount of immunoglobulin secretion was quantitated by ELISA. B cells were purified from Ars/A1 mice and treated with LPS in the presence or absence of ssDNA (500 μg/ml) or Ars$_7$BSA ($10^{-4}$M) (right panel). Cultures were treated with LPS (30 μg/ml) and at day 4, the amount of immunoglobulin secretion was quantitated by ELISA.

Figure 20:
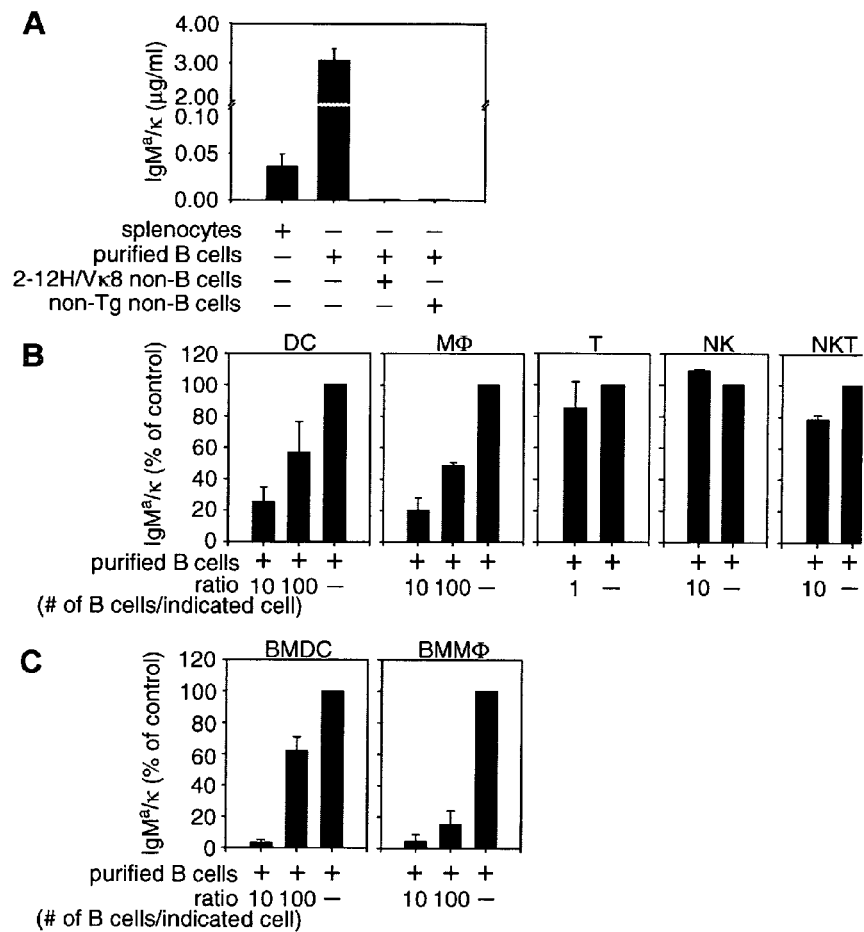

FIG. 20 demonstrates that DCs and MΦs repress Ig secretion by Sm-specific B cells. Splenocytes from 2-12H-Vκ8 mice ($1\times10^5$ B cells) or equal numbers of purified B cells were stimulated with LPS (30 μg/ml) or cocultured with $1\times10^5$ non-B cells from either 2-12H/Vκ8 or non-Tg mice and (A), the indicated ratio of positively selected splenic DCs and MΦ, or sorted T, NK, or NK T cells (B), or BMDCs or BMMΦ from non-Tg mice (C). IgM$^a$/κ levels were quantitated at day 4 by ELISA. LPS-stimulated B cells (100%) secreted 2-10 μg/ml IgM$^a$/κ. Data represent at least 4 experiments.

Figure 21:
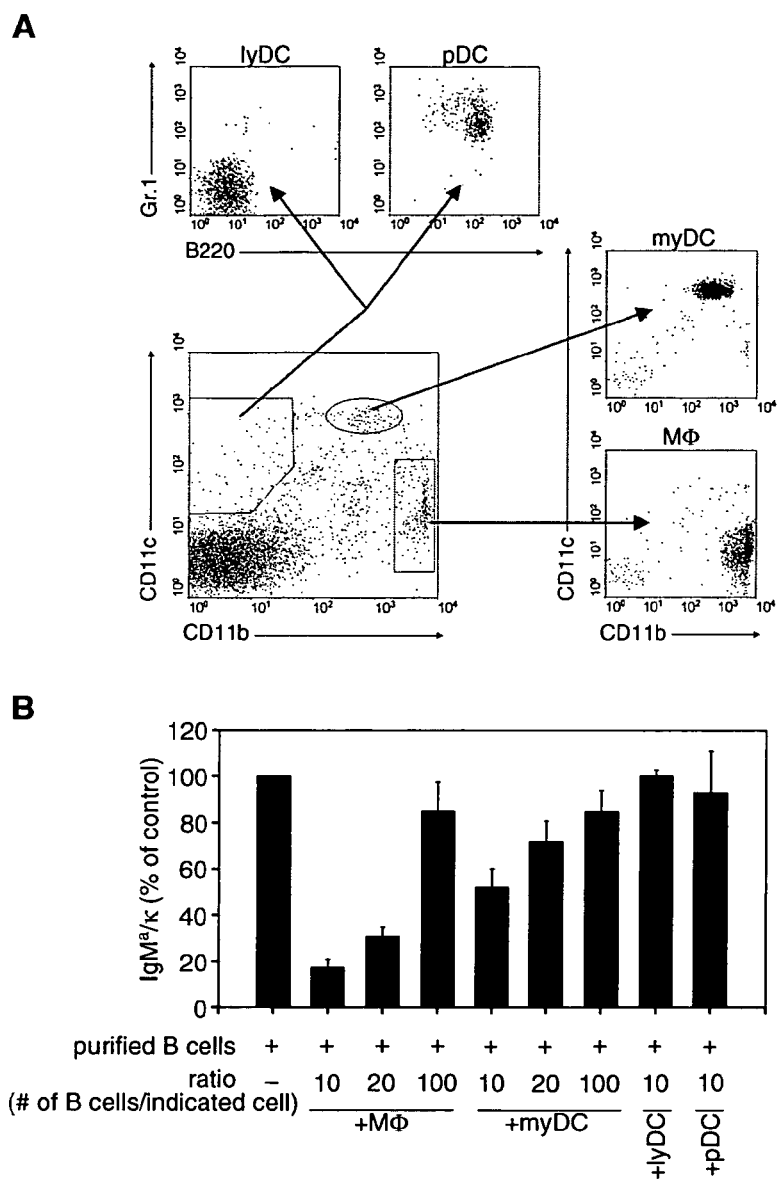

FIG. 21 shows Ig secretion by Sm-specific B cells is repressed by MyDCs and MΦ but not other DC subsets. A, Splenic myDCs, LyDCs, pDCs, and MΦ were sorted based on expression of CD11b, B220, and GR1. B, Various ratios of myDCs, lyDCs, pDCs, and MΦ were cocultured with Sm-specific B cells ($1\times10^5$) and stimulated with LPS (30 μg/ml). IgM$^a$/κ secretion was quantitated by ELISA. LPS-stimulated B cells (100%) secreted 2-25 μg/ml IgM$^a$/κ. Data represent at least three experiments.

DETAILED DESCRIPTION OF THE INVENTION

The immune system responds to foreign antigens by provoking immune responses while simultaneously remaining unresponsive to self-antigens. Although this immunologic discrimination is very efficient, failure of these basic immunoregulatory processes leads to chronic infectious diseases, autoimmune diseases and tumors. Systemic Lupus Erythematosus (SLE) is a systemic autoimmune disease characterized by the production of autoantibodies specific for many nuclear antigens including ssDNA, dsDNA, histones and Smith antigen (Sm). These autoantibodies form immune complexes that cause multi-organ failure. The event(s) that initiate disease remain unclear but tolerance mechanisms such as deletion (dsDNA), B1 formation (Sm), anergy (HEL) and suppression of T helper ($T_H$) cells by T regulatory ($T_{reg}$) cells have been described. Disease is associated with an increased burden of apoptotic cells and onset is often correlated with recent bacterial or viral infections.

Previous studies of the anti-Sm response in SLE showed that Sm-specific B cells remain tolerant by peripheral anergy. The inventors have discovered that anergy of anti-Sm B cells is maintained by a regulatory immune cell population that expresses surface Sm. Removal of the regulatory immune cells "de-repressed" the autoreactive B cells such that subsequent stimulation with LPS induced anti-Sm secretion. These data show that the non-responsive state associated with tolerance to Sm was readily reversed upon removal of a cell population. Further analysis showed that the regulatory immune cell population produced soluble factors in response to LPS stimulation that repressed anti-Sm secretion. The soluble factors repressed secretion of LPS-induced antibodies from antigen experienced cells but were unable to suppress naïve B cells. These findings offer tremendous potential in selectively regulating autoreactive B cells while allowing naïve B cells to maintain immune function.

The inventors have further discovered that nuclear antigens normally expressed by dying cells are displayed on the surface of the regulatory immune cell population. While not wishing to be bound by any particular theory of the invention, ligation of antigen epitopes displayed on regulatory immune cells by B cells expressing surface receptors specific for nuclear antigens provides a mechanism of conjugation between B cells and the regulatory immune cell population. Subsequent activation of the regulatory immune cells, e.g., through Toll Like Receptors (TLR), CD40 receptor and/or TNF receptor (e.g., a TNF-α receptor), induces secretion of a soluble factor(s) that represses the production of autoantibodies by the B cell. These observations are therapeutically beneficial in repressing autoantibody secretion and/or to treat autoimmune disorders. The invention also provides methods of diagnosing defects in individual patients that result in autoantibody secretion and/or autoimmune disease.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Except as otherwise indicated, standard methods known to those skilled in the art may be used for cloning genes, amplifying and detecting nucleic acids, and the like. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

As one aspect, the invention provides an isolated regulatory immune cell. In particular embodiments, the regulatory immune cell is a dendritic cell (DC) or a macrophage (MΦ)). In representative embodiments, the DC is a myeloid DC, and/or a lymphoid DC, plasmacytoid DC. Further, in other embodiments, the MΦ is a marginal zone MΦ, a red pulp MΦ, and/or a metallophilic MΦ. Those skilled in the art will appreciate that the terminology in this area is in flux. The terms "DC" and "MΦ" are intended to encompass cells and subpopulations of cells that are now or later identified that fall within the current understanding and definition of these terms.

As used herein, an "isolated cell" is a cell that has been removed from a subject or is derived from a cell that has been removed from a subject, and has been enriched or at least partially purified from the tissue or organ (e.g., blood, spleen, skin, bone marrow) with which it is associated in its native state.

In particular embodiments, the regulatory immune cell is a splenic cell, a lymph node cell or a peripheral blood cell or is derived from bone marrow stem cells or from CD34 selected stem cells isolated from peripheral blood by leukophoresis or from bone marrow (e.g., a hematopoietic stem cell [HSC]). As a further alternative, monocytes can be isolated from peripheral blood and activated to produce DC and/or MΦ (Sallusto et al., (1994) *J. Exp. Med.* 179:110-1118; Becker et al., (1987) *J. Immunol.* 139:3703-3709).

As described in more detail herein, those skilled in the art will appreciate that the regulatory immune cell can be derived from an isolated precursor cell, such as an isolated HSC or a peripheral blood monocyte. The regulatory immune cell can be derived from the isolated precursor either in vitro or in vivo. In the case that the precursor cell (or regulatory immune cell derived therefrom) is administered to a mammalian subject in accordance with the methods of the invention, the cell can be autologous or heterologous to the mammalian subject.

The regulatory immune cell can display an epitope from a self-antigen on the cell surface. For example, in particular embodiments, the regulatory immune cell can be loaded with apoptotic cells or otherwise display an epitope (e.g., a B cell epitope) from a self-antigen (e.g., a nuclear antigen such as the Sm antigen) on its cell surface. Methods of producing apoptotic cells are known in the art. For example, apoptotic cells can be derived by irradiating peripheral blood mononuclear cells. The apoptotic cells can be derived from the patient to be treated, a normal donor, or an exogenous source. As used herein, a "nuclear antigen" includes but is not limited to components of nucleosomes (e.g., ssDNA, dsDNA, histones) and small nuclear ribonucleoprotein particles (e.g., Sm, nRNP-A, nRNP-C). As known in the art, B cell epitopes are typically conformationally-dependent three-dimensional protein domains that are displayed on the membrane surface, although linear B cell epitopes have been reported. Unlike T cell epitopes, B cell epitopes are not presented on the cell surface by MHC class I/II molecules.

Exemplary self-antigens include DNA, RNA, Sm, Rose antigen (Ro) and Latimer antigen (La), which are implicated in lupus. In anti-phospholipid syndrome, the individual has autoimmunity against cardiolipin, β2-glycoprotein-1 and/or prothrombin. Autoimmunity to muscinergic receptors is found in Sjogren's disease. In pemphigus vulgaris, autoimmunity is mounted against desmoglin proteins (Dsg proteins 1, 3 and/or 4), annexins and/or the acetylcholine receptor.

Autoreactive B cells according to the present invention can display specificity to these or other self-antigens.

Alternatively, the regulatory immune cell can be administered without loading; it appears that the regulatory immune cell can acquire self-surface antigen in vivo (e.g. from apoptotic cells) without loading in vitro.

In particular embodiments, the isolated regulatory immune cells of the invention can be derived from an isolated HSC or peripheral blood monocyte.

Alternatively, or additionally, the cell can be activated (e.g., through a Toll Like Receptor [TLR], CD40 antigen and/or TNF receptor) to secrete a soluble factor(s) or mediator that modulates B cell function, such as repression of autoantibody production and/or secretion by autoreactive B cells.

In particular embodiments, the soluble factor that represses autoantibody secretion by autoreactive B cells comprises, consists of, or consists essentially of a regulatory cytokine. By "consists essentially of" it is meant that the indicated substance does not contain significant amounts of active agent other than the specified active agent.

In representative embodiments, the soluble factor comprises, consists of, or consists essentially of one or more regulatory cytokines that are Tumor Necrosis Factor (TNF) family members. TNF family members include but are not limited to TNF-α, TNF-β, lymphotoxins such as lymphotoxin-α, lymphotoxin-β and LIGHT, 4-1BB ligand, Blys/April, CD27 ligand, CD30 ligand, CD40 ligand (CD40L), Fas ligand, GITR ligand, OX40 ligand, RANK ligand, THANK, TRAIL, TWEAK, VEG1). For a review of the TNF superfamily, see MacEwan, (2002) *Br. J. Pharmacology* 135:855-875.

In other embodiments, the soluble factor comprises, consists essentially of, or consists of one or more regulatory cytokines that can be, for example, selected from the following group: interleukin-1 (IL-1), IL-2, IL-3, IL-4, IL-5, IL-6, IL-7, IL-8, IL-10, IL-12, IL-13, IL-14, IL-15, IL-18, IL-23, IL-24, Il-25, IL-26, Blys/April, TGF-α, TGF-β, interferon-α (IFN-α), IFN-β, IFN-γ, MIP-1, MIF, MCP-1, M-CSF or M-CSF, and/or a TNF family member and/or an analog or small molecule analog of any of the foregoing.

In other embodiments, the soluble factor comprises, consists essentially of, or consists of IL-6, CD40L and/or a TNF family member (e.g., TNF-α).

In other embodiments, the soluble factor is an exosome that is released by the regulatory immune cell.

The regulatory immune cell (and precursors thereof) can be from any species, but is generally a mammalian cell (e.g., a mouse, rat, cow, pig, goat, sheep, cat, dog, horse, rabbit, hamster, human or non-human primate cell). For administration to a subject, the regulatory immune cell (or precursor thereof) is generally from the same species as the subject or is otherwise rendered compatible with the subject.

The invention further provides a cell culture comprising a plurality of the isolated regulatory immune cells of the invention as well as conditioned medium produced by the isolated cells and cell cultures.

As a further aspect, the invention provides methods of repressing autoantibody production and/or secretion by autoreactive B cells. In particular embodiments, the method comprises contacting an autoreactive B cell with an isolated regulatory immune cell and/or a soluble factor(s) as described above that represses autoreactive B cell autoantibody production and/or secretion. The soluble factor can be produced by the regulatory immune cell or can be provided as an exogenous factor. In particular embodiments, the method comprises contacting the autoreactive B cell with a soluble factor comprising IL-6, CD40L and/or a TNF family member (e.g., TNF-α).

The methods of the invention can be practiced to repress autoantibody production and/or secretion by autoreactive B cells in vitro or in vivo. By "repress," "represses," "repressed" or "repression" (and grammatical variations thereof) it is meant a reduction (e.g., by at least about 20%, 25%, 30%, 40%, 50%, 60%, 70%, 80%, 90%, 95%, 98% or more) in the level of autoantibody production and/or secretion, e.g., as compared with the level of production and/or secretion prior to the indicated treatment or as compared with an untreated or control cell. The terms "repress," "represses," "repressed" or "repression" (and grammatical variations thereof) can also indicate delay, prevention, and/or a reduction (as defined above) in the onset of autoantibody production and/or secretion.

The terms "contacting" and "contact" and grammatical variants thereof are intended broadly and encompass interactions between the autoreactive B cell and regulatory immune cell and/or soluble factor in vitro or in vivo. As an alternative, in some embodiments, the isolated regulatory immune cell and/or soluble factor is administered to the subject and contacted with the B cell in vivo. For example, the B cell and the isolated regulatory immune cell and/or soluble factor can be incubated or cultured together in vitro.

In particular embodiments, the autoreactive B cell is contacted in vivo with the isolated regulatory cell and/or soluble factor after administration of the cell and/or soluble factor to a mammalian subject. When contacted in vivo, the mammalian subject is optionally in need of repression of autoreactive B cell autoantibody production and/or secretion, for example, because the subject is suspected of having or has been diagnosed as having autoimmune disease or is at risk for autoimmune disease or has, is diagnosed with or is at risk for any other condition that results from aberrant autoantibody production and/or secretion by autoreactive B cells.

Thus, in representative embodiments, the invention provides a method of repressing B cell autoantibody secretion, the method comprising contacting an autoreactive B cell with an isolated regulatory cell of the invention and/or a soluble factor that represses B cell autoantibody secretion (both as described herein). The isolated cell can be activated in vitro and/or in vivo to secrete a soluble factor that represses B cell autoantibody secretion. The cell can be activated through a TLR, CD40 antigen and/or a TNF receptor (e.g., TNF-α receptor). The isolated cell can be administered to a mammalian subject and then activated in vivo. Alternatively, the isolated cell is activated in vitro and is then administered to a mammalian subject. Optionally, the isolated cell is further activated in vivo. As a further alternative, the isolated cell is not activated by external manipulations. According to this embodiment, the cell is activated in vivo in response to naturally occurring factors (e.g., through a TLR in response to bacterial or viral infection).

In certain embodiments, the invention is practiced to treat autoimmune disease. By the terms "treat," "treating," "treats" or "treatment of" (and grammatical variations thereof), it is intended that the severity or onset of the condition is reduced, delayed, prevented or at least partially improved or modified and that some alleviation, mitigation or decrease in at least one clinical symptom is achieved.

As used herein, a "treatment-effective" amount or "an amount effective to treat" (and grammatical equivalents) is an amount that provides some improvement or benefit to the subject. Alternatively stated, a "treatment-effective" amount is an amount that provides some alleviation, mitigation, or decrease in at least one clinical symptom of autoimmune disease and/or aberrant B cell autoantibody secretion as is well-known in the art (e.g., decreased ANA titer, decreased immune complex deposition in the kidney, decreased inflammation of the skin and kidney, and the like). Those skilled in the art will appreciate that the therapeutic effects need not be complete or curative, as long as some benefit is provided to the subject.

In particular embodiments of treating autoimmune disease, the method comprises administering to a mammalian subject in a treatment-effective amount an isolated regulatory immune cell and/or a soluble factor(s) as described above that represses B cell autoantibody production and/or secretion. In particular embodiments, the method comprises administering a soluble factor comprising IL-6, CD40L and/or a TNF family member (e.g., TNF-α). Optionally, the mammalian subject is a subject in need of treatment for autoimmune disease, e.g., because the subject is suspected of having or has been diagnosed as having autoimmune disease or is at risk for autoimmune disease.

In other representative embodiments, the method of treating autoimmune disease comprises administering to a mammalian subject in a treatment effective amount an isolated regulatory immune cell of the invention. In other representative embodiments, the method comprises administering to a mammalian subject in a treatment-effective amount an isolated regulatory immune cell and a soluble factor (as described above) that represses B cell autoantibody secretion. In still further embodiments, the method comprises administering a soluble factor that represses B cell autoantibody secretion to the mammalian subject.

Thus, as particular aspects, the invention provides methods of treating an autoimmune disease in a mammalian subject, the method comprising administering to the mammalian subject a treatment-effective amount of an isolated regulatory cell of the invention and/or a soluble factor that represses B cell autoantibody secretion (both as described herein). The isolated cell can be from the mammalian subject (e.g., is autologous to the subject) or can be from a donor subject (e.g., heterologous to the mammalian subject). The isolated cell can be activated in vitro or in vivo to produce a soluble factor that represses B cell autoantibody secretion (e.g., through a TLR, CD40 antigen and/or a TNF receptor [such as a TNF-α receptor]). The isolated cell can be activated in vivo after administration to the mammalian subject. Alternatively, the isolated cell can be activated in vitro and then administered to the mammalian subject. Optionally, the cell can be further activated in vivo after administration to the subject. As a further alternative, the isolated cell is not activated by external manipulations. According to this embodiment, the cell is activated in vivo in response to naturally occurring factors (e.g., through a TLR in response to bacterial or viral infection).

In still other embodiments, the invention provides methods of treating autoimmune disease, the method comprising removing B cells from the subject, contacting the B cells with the isolated regulatory immune cell(s) and/or soluble factor in vitro, and then administering the B cells back to the subject (optionally, the isolated cell and/or soluble factor is administered to the subject as well). As used herein, methods that comprise "removing B cells" (and like terms) encompass methods of removing cells or tissue that comprise B cells in addition to methods of selectively removing enriched or purified B cell populations from the subject.

The soluble factor can be a purified factor (e.g., a recombinant factor, a factor isolated from natural sources and/or a synthetic peptide), present in conditioned medium and/or can be secreted by a regulatory immune cell or cell culture. For example, the autoreactive B cell can be cultured with an isolated regulatory immune cell of the invention and can be contacted with soluble factor secreted by the cell without necessarily being in contact with the cell. Likewise, the isolated regulatory immune cell of the invention can be administered to a subject and the autoreactive B cell contacted with soluble factor produced by the isolated cell without necessarily being in contact with the isolated cell or cell culture.

As a further possibility, endogenous regulatory immune cells (i.e., not isolated) can be activated to produce a soluble factor that represses B cell autoantibody secretion (as described herein), and the soluble factor can contact the B cell without the endogenous activated regulatory immune cells necessarily being in contact with the B cell. As still another alternative, the soluble factor can be provided in vivo by administering a nucleic acid that is expressed to produce the soluble factor. Methods of administering nucleic acids expressing proteins and peptides are well-known in the art.

According to the present invention, the autoreactive B cell can be any B cell or, alternatively, can be from a subpopulation of B cells and further can have any specificity against self-antigen. For example, the B cells can be, without limitation, antibody secreting cells [ASC] including plasma cells, plasmablasts, marginal zone cells, B1 cells, transitional B cells and/or follicular B cells.

Isolated or endogenous regulatory immune cells are optionally activated to secrete a soluble factor (as described herein) that represses autoreactive B cell autoantibody production and/or secretion. The regulatory immune cell can be activated in vitro and/or in vivo to secrete the soluble factor by any method known in the art. In particular embodiments, the regulatory immune cell is activated through a TLR receptor (e.g., TLR2, TLR3, TLR4, TLR5, TLR6, TLR7, TLR8 and/or TLR9), CD40 antigen and/or a TNF (e.g., TNF-$\alpha$) receptor. Alternatively, the isolated or endogenous regulatory immune cell can be left to be activated by naturally occurring factors, e.g., by TLR ligation upon bacterial or viral infection. According to the methods of the invention, isolated regulatory immune cells can be autologous or heterologous to the B cell and/or the mammalian subject.

Numerous activators or agonists of TLRs are known in the art including but not limited to viral or bacterial products (e.g., lipopolysaccharide [LPS]), peptidoglycans, lipopeptides, apoptotic cells, activating CpG nucleic acids (i.e., nucleic acids such as DNA containing CpG motifs, which are generally understood to be unmethylated cytosine-guanine [GC] dinucleotides within a flanking base motif), Immune Response Modifier (IRM) compounds, flagellins, Mycoplasma MALP-2, polyIC (polyinosinic-polycytidylic acid), and compound R848. TLRs are a family of type I transmembrane receptors characterized by an extracellular amino terminus. They have an amino-terminal leucine-rich repeat (LRR) domain and a carboxy-terminal intracellular tail containing a conserved region called the Toll/interleukin-1 receptor (TIR) homology domain. The extracellular domain contains a varying number of LRR domains, which may be involved in ligand binding but may also be necessary for TLR dimerization. Consistent with their role in pathogen recognition, TLR family members are expressed by cells involved in the first line of host defense, including neutrophils, M$\Phi$, DC, dermal endothelial cells and mucosal epithelial cells. A variety of chemically diverse pathogen-associated molecular patterns are now known to be TLR agonists. For example, Mycoplasma MALP-2, mycobacterial LAM, yeast Zymozan, and lipoproteins from gram positive bacteria are agonists of TLR2; TLR3 is agonized by dsRNA and polyIC; RSV protein F, LPS from gram negative bacteria, and host-derived Hsp60, fibronectin, and hyluronan are agonists of TLR4; certain flagellins are agonistic to TLR5; imidazoquinoline compounds and R848 are agonistic to TLR7, and bacterial CpG DNA is agonistic to TLR9 (Armant and Fenton (2002) *Genome Biology* 3: 3011.1-3011.6).

In certain embodiments, the TLR agonist can be a natural agonist of a TLR or a synthetic IRM compound. An IRM compound generally refers to a compound that alters the level of one or more immune regulatory molecules, e.g., cytokines or co-stimulatory markers, when administered to an IRM-responsive cell.

Certain IRMs that are useful as TLR agonists in the methods of the invention are small organic molecules (e.g., molecular weight less than about 1000 Daltons, and less than about 500 Daltons in some cases). Certain small molecule IRM compounds are disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; and 6,573,273; European Patent 0 394 026; U.S. Patent Publication No. 2002/0055517; and International Patent Publication Nos. WO 01/74343; WO 02/46188; WO 02/46189; WO 02/46190; WO 02/46191; WO 02/46192; WO 02/46193; WO 02/46749 WO 02/102377; WO 03/020889; WO 03/043572 and WO 03/045391.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain benzimidazole derivatives (such as those described in U.S. Pat. No. 6,387,938), and certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/085905).

Other IRMs include large biological molecules such as oligonucleotide sequences. Some IRM oligonucleotide sequences contain CpG motifs and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Small molecule IRM compounds suitable for use as a TLR agonist in the practice of the invention include compounds having a 2-aminopyridine fused to a five membered nitrogen-containing heterocyclic ring. Such compounds include, for example, imidazoquinoline amines including but not limited to substituted imidazoquinoline amines such as, for example, aminoalkyl-substituted imidazoquinoline amines, amide-substituted imidazoquinoline amines, sulfonamide-substituted imidazoquinoline amines, urea-substituted imidazoquinoline amines, aryl ether-substituted imidazoquinoline amines, heterocyclic ether-substituted imidazoquinoline amines, amido ether-substituted imidazoquinoline amines, sulfonamido ether-substituted imidazoquinoline amines, urea-substituted imidazoquinoline ethers, and thioether-substituted imidazoquinoline amines; tetrahydroimidazoquinoline amines including but not limited to amide-substituted tetrahydroimidazoquinoline amines, sulfonamide-substituted tetrahydroimidazoquinoline amines, urea-substituted tetrahydroimidazoquinoline amines, aryl ether-substituted tetrahydroimidazoquinoline amines, heterocyclic ether-substituted tetrahydroimidazoquinoline amines, amido ether-substituted tetrahydroimidazoquinoline amines, sulfonamido ether-substituted tetrahydroimidazoquinoline amines, urea-substituted tetrahydroimidazoquinoline ethers, and thioether-substituted tetrahydroimidazoquinoline amines; imidazopyridine amines including but not limited to amide-substituted imidazopyridine amines, sulfonamido-substituted imidazopyridine amines, urea-substituted imidazopyridine amines; aryl ether-substituted imidazopyridine amines, heterocyclic ether-substituted imidazopyridine amines, amido ether-substituted imidazopyridine amines, sulfonamido ether-substituted imidazopyridine amines, urea-substituted imidazopyridine ethers, and thioether-substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; and thiazolonaphthyridine amines.

In certain embodiments, the TLR agonist is an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and/or a thiazolonaphthyridine amine.

In other embodiments, the TLR agonist is a sulfonamide-substituted imidazoquinoline amine. In alternative embodiments, the TLR agonist is a urea-substituted imidazoquinoline ether. In another alternative embodiment, the TLR agonist is an aminoalkyl-substituted imidazoquinoline amine.

In one particular embodiment, the TLR agonist is 4-amino-α,α,2-trimethyl-1H-imidazo[4,5-c]quinolin-1-ethanol. In an alternative particular embodiment, the TLR agonist is N-(2-{2-[4-amino-2-(2-methoxyethyl)-1H-imidazo[4,5-c]quinolin-1-yl]ethoxy-}ethyl)-N-methylmorpholine-4-carboxamide. In another alternative embodiment, the TLR agonist is 1-(2-amino-2-methylpropyl)-2-(ethoxymethyl-)-1H-imidazo[4,5-c]quinolin-4-amine. In another alternative embodiment, the TLR agonist is N-[4-(4-amino-2-ethyl-1H-imidazo[4,5-c]quinolin-1-yl)-butyl]methanesulfonamide. In yet another alternative embodiment, the TLR agonist is N-[4-(4-amino-2-propyl-1H-imidazo[4,5-c]quinolin-1-yl)butyl]methanesulfonamide.

In certain alternative embodiments, the TLR agonist is a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and/or a thiazolonaphthyridine amine.

As used herein, a substituted imidazoquinoline amine refers to an aminoalkyl-substituted imidazoquinoline amine, an amide-substituted imidazoquinoline amine, a sulfonamide-substituted imidazoquinoline amine, a urea-substituted imidazoquinoline amine, an aryl ether-substituted imidazoquinoline amine, a heterocyclic ether-substituted imidazoquinoline amine, an amido ether-substituted imidazoquinoline amine, a sulfonamido ether-substituted imidazoquinoline amine, a urea-substituted imidazoquinoline ether, or a thioether-substituted imidazoquinoline amines. In particular embodiments, the substituted imidazoquinoline amine specifically and expressly excludes 1-(2-methylpropyl)-1H-imidazo[4,5-c]quinolin-4-amin-e and 4-amino-α,α-dimethyl-2-ethoxymethyl-1H-imidazo[4,5-c]qui-nolin-1-ethanol.

TLR6 and TLR7 agonists are known in the art and include without limitation compounds comprising an imidazopyridine amine, an imidazonaphthyridine amine, an imidazotetrahydronaphthyridine amine, a thiazoloquinoline amine, an oxazoloquinoline amine, a 1,2-bridged imidazoquinoline amine, a thiazolonaphthyridine amine, an imidazothienopyridine, a sulfonamido-substituted imidazoquinoline amine, a urea-substituted imidazoquinoline amine, a heteroaryl ether-substituted imidazoquinoline amine, N-[4-(4-amino-2-ethyl-1H-[4,5-c]quinolin-1-yl)but-yl]methanesulfonamide, or 4-amino-2-(ethoxymethyl)-α,α,-dimethyl-6,7,8,9-tetrahydro-1H-imidazo[4,5-c]quinolin-1-ethanol hydrate.

Further, compounds that are selective TLR7 and TLR8 activators are disclosed in U.S. Publication No. 20040171086 (the disclosure of which is incorporated herein by reference in its entirety).

Other TLR agonists are described in U.S. Patent Publication Nos. 20040171086; 20040141950; and 20040014779.

Methods of identifying other TLR agonists are known in the art and include methods described in U.S. Patent Publication Nos. 20040132079; 20030166001; 20040171086; 20040141950; and 20040014779.

Agonists of CD40 antigen are also well-known in the art and include CD40L (CD40 Ligand); see, e.g., Armitage et al. (1992) *Nature* 357:80 and Spriggs et al., *J. Exp. Med.* (1992) 176:1543) and anti-CD40 antigen antibodies.

CD40L (also referred to as CD154) is a known ligand for CD40. Recombinant soluble CD154 (rsCD154) composed only of the extracellular, receptor-binding domain of CD154 is a functional agonist (Armitage, (1993) *Eur. J. Immunol.* 23:2326-2331; Lane, (1993) *J. Exp. Med.* 177:1209-1213). However, rsCD154 is not as effective as native CD154 expressed on the cell membrane to induce CD40 signaling because optimal signaling requires multimerization of the CD40 receptors at the cell surface (Schwabe et al., (1997) *Hybridoma* 16:217-226). As a result, ligand-multimerization domains have been engineered, such as leucine zippers or CD8 domains, onto the N-terminal domain of rsCD154 to enhance receptor signaling. (Lans et al., (1993) *J. Exp. Med.* 177:1209-1213; Morris, (1999) *J. Biol. Chem.* 274:418-423). Novel chimeric CD154 polypeptides are taught in U.S. patent application Ser. No. 10/154,759.

Agonistic monoclonal antibodies against CD40 antigen are also known (see, e.g., Mauri, (2000) *Nature Med.* 6:673-679). Francisco et al. ((2000) *Cancer Research* 60:3225-3231) demonstrate agonistic properties and in vivo antitumor activity of an anti-CD40 antibody, SGN-14. Anti-CD40 antibodies are available from commercial sources.

TNF receptor agonists (e.g., TNF-α, TNF-β and anti-TNF receptor antibodies) are also known in the art and can be used for cell activation. TNF receptors TNF-R1 (also called p55 or p60) and TNFR-2 (p75 or p80) are both involved in eliciting the effects of the cytokine TNF-α. Both polyclonal and monoclonal antibodies directed against TNF-R1 can act as specific agonists for this receptor and elicit TNF activities such as cytotoxicity, fibroblast proliferation, resistance to Chlamydiae, and synthesis of prostaglandin $E_2$ (Engelmann et al., (1990) *J. Biol. Chem.* 265:14497; Espevik et al., (1990) *J. Exp. Med.* 171:415; Shalaby et al., (1990) *J. Exp. Med.* 172:1517; Pang et al., (1996) *Thyroid* 6:313).

According to the inventive methods of repressing B cell autoantibody production and/or secretion, the B cell can be contacted with the isolated cell and/or soluble factor in vitro or in vivo. Likewise, in methods of treating autoimmune disease, the isolated cell and/or soluble factor can be administered to the subject or alternatively, the method can involve ex vivo manipulation of B cells from the subject.

In practicing the methods of the invention, the regulatory immune cell can be autologous to the B cell and the mammalian subject (for example, is isolated or derived from the same mammalian subject or is an endogenous regulatory immune cell). Alternatively, the regulatory immune cell can be heterologous (i.e., foreign or exogenous) to the B cell and the mammalian subject.

Further, as described herein, the regulatory immune cell can optionally be activated in vitro and/or in vivo to secrete a soluble factor that represses B cell autoantibody production and/or secretion (e.g., through a TLR, CD40 antigen or TNF receptor mediated pathway).

In some embodiments, the isolated regulatory immune cell is heterologous to the B cell and the mammalian subject. For example, the isolated regulatory immune cell can be derived from a donor (e.g., a healthy subject) or from cultured cells. The heterologous cells are optionally selected to be Major Histocompatibility Complex class I (MHC-I) compatible with the recipient. In particular embodiments, the heterologous regulatory immune cell is loaded with cells from the recipient and thereby displays the recipient's MHC-I molecules on the surface. As a further alternative, the heterologous regulatory immune cell is MHC class I/II deficient.

As described herein, the heterologous regulatory immune cell can be activated in vitro to secrete a factor that represses B cell autoantibody production and/or secretion (for example, by administering a compound that activates a TLR, CD40 antigen and/or TNF receptor) and administered to the subject. Optionally, the heterologous regulatory immune cells are further activated in vivo after administration to the subject.

Alternatively, the heterologous regulatory immune cell can be administered to the subject without in vitro activation and is optionally activated in vivo after administration to the subject.

In other embodiments, the regulatory immune cells can be removed from a subject, activated in vitro to secrete a soluble factor that represses B cell autoantibody secretion and optionally administered back to the subject. The regulatory immune cell can further be activated in vivo to secrete a soluble factor that represses B cell autoantibody production and/or secretion (e.g., by administering a compound that activates a TLR, CD40 antigen or TNF receptor mediated pathway). In particular embodiments, the method encompasses methods of removing a cell from a subject, culturing it under conditions that cause the cell to differentiate, dedifferentiate or otherwise acquire a desirable property (e.g., culturing bone marrow-derived HSCs peripheral blood monocytes under conditions that result in differentiation to produce DC or MΦ).

Those skilled in the art will appreciate that in the methods of the present invention, "removing a cell from a subject" (or similar expressions) and "administration of the cell" (or similar expressions) to the same or another subject, and the like, encompasses methods that involve culturing the removed cell, e.g., to cause the cell to differentiate, dedifferentiate, to otherwise acquire a desirable property and/or to increase cell number. Thus, as used herein, removing a cell from a subject and then administering the cell to the same or a different subject does not exclude culturing the cell prior to administering it to the subject.

In other embodiments, the regulatory immune cell is removed from the subject, subjected to any desired in vitro manipulation and then re-administered to the mammalian subject. According to this embodiment, the regulatory immune cells are optionally activated in vivo after administration to the subject (for example, by administering to the subject a compound that activates a TLR, CD40 antigen and/or TNF receptor).

As a further alternative, endogenous regulatory immune cells are activated in vivo (as described herein) without removal and ex vivo manipulation of the regulatory immune cell (e.g., the cells are activated in situ).

In other particular embodiments, heterologous or autologous regulatory immune cells are administered to the subject without activation in vitro or in vivo.

As used herein, the term "autoimmune disease" refers to a condition that results from, or is aggravated by, the production by B cells of antibodies that are reactive with normal body tissues. It is a condition in which the immune system mistakenly attacks the body's own organs and tissues. In particular embodiments, the autoimmune disease is one that involves secretion of an autoantibody that is specific for an epitope from a self antigen (e.g., a nuclear antigen).

Autoimmune diseases that can be treated according to the present invention include, but are not limited to immune complex disorders such as those that result in glomerulonephritis, Goodpasture's syndrome, necrotizing vasculitis, lymphadenitis, peri-arteritis nodosa and systemic lupus erythematosis. Other illustrative autoimmune diseases include but are not limited to systemic lupus erythematosis, glomerulonephritis, Goodpasture's syndrome, necrotizing vasculitis, peri-arteritis nodosa (i.e., polyarthritis), rheumatoid arthritis, psoriatic arthritis, psoriasis, systemic sclerosis, anti-phospholipid antibody syndrome, pemphigus vulgaris, ANCA-associated vasculitis (e.g., Wegener's granulomatosis, microscopic polyangiitis), Sjogren's syndrome, Crohn's disease, and Hashimoto's thyroiditis.

One advantage of the methods of the invention as compared with traditional methods of treating autoimmune disease is that the inventive methods can be relatively specific for autoreactive B cells and have less impact on naïve B cells or B cells of other specificities (e.g., which are generally either naïve or only acutely antigen experienced). In particular embodiments, the autoreactive B cell has been subjected to chronic antigen experience. Thus, the invention can be practiced to preferentially target chronically antigen experienced autoreactive B cells.

The inventive methods of repressing autoreactive B cell autoantibody secretion and/or treating an autoimmune disease can be carried out in conjunction with any other methods known in the art for repressing autoantibody secretion and/or treating an autoimmune disease. To illustrate, in representative embodiments, the method further comprises depleting B cells in the subject by administering a B cell depletion therapy. By the terms "deplete," "depletion," "depleting," and grammatical variations thereof, it is meant that there is a reduction of at least about 25%, 35%, 50%, 60%, 75%, 80%, 85%, 90%, 95%, 98%, 99% or more in the number of B cells, optionally autoreactive B cells, or in a particular subpopulation(s) of B cells (e.g., antibody secreting cells [ASC] including plasma cells, plasmablasts, marginal zone cells, B1 cells, transitional B cells and/or follicular B cells).

B cell depletion can be achieved by any of the numerous methods now known in the art or later discovered. For example, the subject can be treated by chemotherapy, radiation therapy, radioimmunotherapy and/or immunotherapy. In particular embodiments, B cells are depleted by administering to the mammalian subject in a treatment-effective amount a composition that depletes B cells. In some embodiments, the composition comprises an antibody or ligand that specifically binds to an epitope on B cells (e.g., a B cell specific epitope). For example, the antibody can be an anti-CD20 antibody (e.g., Rituximab). The antibody can be administered by any method known in the art, e.g., by infusion.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., *Molec. Immunol.* 26, 403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Monoclonal antibodies can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246, 1275-81.

Antibodies specific to B cell epitopes can also be obtained by phage display techniques known in the art or by immunizing a heterologous host with a cell containing an epitope of interest (e.g., B cells).

In other embodiments, tissue, cells or body fluid comprising B cells is removed from a subject (e.g., blood, bone marrow, spleen or lymph nodes or lymph fluid are removed from the subject), and the B cells in the tissue, cells or body fluid are depleted by any method known in the art (e.g., by immunopurification techniques or plasmaphoresis of blood to remove B cells), and then the B-depleted tissue, cells or fluid administered back to the subject.

B cell depletion can be carried out prior to, concurrently with, or following the methods set forth above (e.g., regulatory cell and/or regulatory cytokine based therapy). In particular embodiments, B cell depletion is commenced (i.e., initiated) prior to the foregoing methods based on regulatory cell and/or regulatory cytokine therapy. In other representative embodiment, B cell depletion protocols are completed prior to commencing the regulatory cell-based and/or regulatory cytokine-based methods of the invention. In illustrative methods, a course of therapy for a subject comprises short-term (e.g., not chronic; for example, treatment every 2, 3 or 4 weeks or once, twice, three or four times a week or even daily for a period from about one, two or three weeks to about four, six, eight, ten, twelve or 16 weeks) treatment to deplete B cells, followed by treatment with the regulatory cell and/or regulatory cytokine based methods of the invention.

The invention further encompasses methods of activating a regulatory immune cell (as described above) to produce a soluble factor (also as described above) that represses B cell autoantibody production and/or secretion. As discussed above, the cell can be activated by any method known in the art, e.g., by contacting the cell with a compound that activates the regulatory cell through a TLR receptor, CD40 antigen and/or TNF receptor (e.g., TNF-α). The method can be practiced in vitro or in vivo (e.g., the compound that activates the regulatory cell can be administered in vivo to activate endogenous regulatory immune cells).

As another aspect, the invention provides methods of treating autoimmune disease and/or repressing B cell autoantibody production and/or secretion in a subject (optionally a subject in need of such treatment), e.g., by administering to the subject a compound that activates a regulatory immune cell to produce a soluble factor that represses autoreactive B cell autoantibody production and/or secretion through a TLR receptor, CD40 antigen and/or TNF receptor (e.g., TNF-α receptor). Exemplary activating compounds are described in more detail above. This aspect of the invention can be practiced to activate endogenous regulatory immune cells or in combination with cell therapy (e.g., to activate donor cells administered to the subject).

The invention also provides a method of repressing B cell autoantibody secretion in a mammalian subject, the method comprising administering to the mammalian subject a soluble factor that represses B cell autoantibody production and/or secretion in an amount effective to repress B cell autoantibody secretion. The invention further provides a method of treating an autoimmune disease in a mammalian subject, the method comprising administering to the mammalian subject a soluble factor that represses B cell autoantibody production and/or secretion in an amount effective to treat the autoimmune disease. The soluble factor can be administered to directly regulate endogenous B cells in situ or can be administered in combination with cell therapy approaches and/or approaches to activate endogenous regulatory immune cells.

As discussed above, those skilled in the art will appreciate that the present invention can also be practiced using cells that are precursors to the regulatory immune cells. The precursor cell can be an isolated cell or a cell in situ. Suitable precursor cells include HSC and peripheral blood monocytes. HSC are particularly desirable because they can colonize the bone marrow of the subject and provide a renewable source of the regulatory immune cell. Further, HSC can be provided in the form of a bone marrow transplant. Bone marrow transplantation methods are known in the art and can be myeloablative or non-myeloablative (e.g., by irradiation).

Thus, the invention encompasses methods of repressing B cell autoantibody secretion in a mammalian subject, the methods comprising administering a plurality of precursor cells (e.g., HSC) that can differentiate into regulatory immune cells (e.g., DC such as myeloid DC and/or MΦ) to the mammalian subject in an amount effective to repress B cell autoantibody secretion in the mammalian subject.

The invention also provides a method of repressing B cell autoantibody secretion in a mammalian subject, the method comprising: culturing a plurality of precursor cells (e.g., HSC) under conditions sufficient for the HSC to differentiate into regulatory immune cells (e.g., DC such as myeloid DC and/or MΦ); and administering a plurality of the regulatory immune cells to the mammalian subject in an amount effective to repress B cell autoantibody secretion in the mammalian subject.

Autoreactive B cells are as described elsewhere herein.

The precursor cells can also be employed in methods of treating autoimmune disease. For example, in representative embodiments, the invention provides a method of treating an autoimmune disease in a mammalian subject, the method comprising administering a plurality of precursor cells (e.g., HSC) that can differentiate into regulatory immune cells (e.g., DC such as myeloid DC and/or MΦ) to the mammalian subject in an amount effective to treat the autoimmune disease.

The invention further provides a method of treating an autoimmune disorder in a mammalian subject, the method comprising culturing a plurality of precursor cells (e.g., HSC) under conditions sufficient for the HSC to differentiate into regulatory immune cells (e.g., DC such as myeloid DC and/or MΦ); and administering a plurality of the regulatory immune cells to the mammalian subject in an amount effective to treat the autoimmune disorder.

Autoimmune diseases are as described elsewhere herein. In particular embodiments, methods of treating autoimmune disorders further comprise administering to the mammalian subject a treatment-effective amount of a B cell depletion therapy (also as described as more detail herein).

In the case of HSC, the HSC can be isolated or, alternatively, the mammalian subject can be given a bone marrow transplant, where the bone marrow transplant comprises the HSC.

Methods of inducing peripheral blood monocytes and HSC to differentiate into DC and/or MΦ are known in the art. For example, GM-CSF and M-CSF induce HSC to differentiate into DC (e.g., myeloid DC) or MΦ, respectively. Monocytes can be cultured in the presence of GM-CSF and/or M-CSF and IL-4 to induce them to differentiate into DC and/or MΦ. The precursor cell can be subjected to appropriate conditions (e.g., in culture) to promote differentiation as known by those skilled in the art. For example, the precursor cells can be cultured under suitable conditions for about 6 to 12, 24, 36, hours or 2, 3, 4, 5, 6, 7, 8, 9 or 10 days, or for about 1 to about 2, 3, 4, 5, 6, 7, 8, 9 or 10 days, or for about 3 days to about 5, 6, 7, 8, 9 or 10 days.

In particular embodiments, HSC are administered to the mammalian subject and the method further comprises administering GM-CSF and/or M-CSF to the mammalian subject to induce the administered HSC to differentiate into the regulatory immune cells. Alternatively, the plurality of HSC can be committed in vitro to the dendritic cell (e.g., myeloid DC) and/or MΦ lineage and are then administered to the mammalian subject. In general, cells commit to differentiate to a particular lineage prior to actually expressing all of the markers and phenotypic characteristics associated with differentiation. To illustrate, short-term exposure (e.g., for about 6 to 12, 18, 24 or 48 hours) of HSC to GM-CSF and/or M-CSF in vitro prior to administration can promote differentiation in vivo after administration while also minimizing the extent and duration of ex vivo manipulations and thereby enhancing the viability of the cells after administration. According to this embodiment, the method can further comprise administering GM-CSF and/or M-CSF to the mammalian subject to induce the administered HSC to differentiate into regulatory immune cells.

As a further option, the precursors are administered and then differentiate in vivo to produce regulatory immune cells without external manipulations.

According to the present invention, it is not necessary that all, or even most, of the precursor cells commit or differentiate as long as the desired effect is achieved. It will be appreciated by those skilled in the art that in a population of precursor cells, not all of the cells will commit or differentiate, or may differentiate to a varying extents. In particular embodiments, at least about 30, 40, 50, 60, 70, 80, 90, 95, 97, 98, 99% or more of the cells commit or differentiate.

In particular embodiments, the method further comprises administering to the mammalian subject an agent that activates the regulatory immune cell through a TLR, CD40 antigen and/or a TNF receptor to secrete a soluble factor that represses B cell autoantibody secretion. Thus, in the case that a precursor cell is administered (committed or not), once the cell differentiates into a regulatory immune cell, it can be activated. If the precursor cell is differentiated in vitro to produce the regulatory cell, which is then administered to the subject, the regulatory cell can be directly activated. Methods of activating regulatory immune cells and soluble factors that repress B cell autoantibody production and/or secretion are as described in more detail herein.

The precursor cell can be autologous to the autoreactive B cell and/or to the mammalian subject. Alternatively, the precursor cell can be from a donor and is heterologous to the B cell and/or to the mammalian subject.

In particular embodiments, the methods further comprise administering to the subject a soluble factor that represses B cell autoantibody production and/or secretion. To illustrate, in particular embodiments, IL-6, CD40L and/or a TNF family member (e.g., TNF-α) is administered to the subject.

Endogenous precursor cells (e.g., HSC in situ) can also be targeted to promote differentiation to regulatory immune cells. Thus, in an exemplary embodiment, the invention provides a method of repressing B cell autoantibody secretion in a mammalian subject, the method comprising administering GM-CSF and/or M-CSF to the mammalian subject in an amount effective to repress B cell autoantibody secretion (e.g., by promoting HSC in the bone marrow to differentiate into regulatory immune cells).

The invention also provides a method of treating an autoimmune disorder in a mammalian subject, the method comprising administering GM-CSF and/or M-CSF to the mammalian subject in an amount effective to treat the autoimmune disorder. According to this embodiment, the GM-CSF and/or C-CSF is promoting the differentiation of precursor cells (e.g., HSC) to the regulatory immune cell.

GM-CSF and/or M-CSF can also be administered to a subject in conjunction with administration of HSC to the subject.

According to these aspects of the invention, the methods can further comprise administering to the mammalian subject an agent that activates regulatory immune cells to secrete a soluble factor that represses B cell autoantibody secretion (e.g., through a TLR, CD40 antigen and/or a TNF receptor [such as a TNF-α receptor]). Thus, once the endogenous precursor has differentiated to produce regulatory immune cells, the regulatory immune cells can be activated.

In particular embodiments, the methods further comprise administering to the subject a soluble factor that represses B cell autoantibody production and/or secretion. To illustrate, in particular embodiments, IL-6, CD40L and/or a TNF family member (e.g., TNF-α) is administered to the subject.

Thus, the methods of the invention can be practiced to repress autoreactive B cell autoantibody production and/or secretion and/or to treat an autoimmune disorder by a number of approaches. For example, a cell-based approach can be used in which donor cells are administered to the subject. The donor cell can be a regulatory immune cell or a precursor thereof (e.g., HSC). In the case of a precursor cell, the cell can be differentiated into the regulatory immune cell, or committed to differentiate, in vitro and then administered. Alternatively, the precursor cell can be administered to the subject. Further, the regulatory immune cell can be activated in vitro and/or in vivo to produce soluble factor that represses B cell autoantibody production and/or secretion. Further, the subject's own regulatory immune cells can be removed and manipulated ex vivo (e.g., activated) and then administered back to the subject. Cell-based approaches can be combined with administration of an exogenous soluble factor that represses B cell autoantibody production and/or secretion. As another approach, the invention can be practiced to activate endogenous regulatory immune cells in situ to produce a soluble factor that represses B cell autoantibody production and/or secretion. Alternatively, endogenous precursor cells (e.g., HSC) can be induced to differentiate into regulatory immune cells (e.g, by administration of GM-CSF and/or M-CSF), which can optionally be activated. As yet another option, a soluble factor(s) that represses B cell autoantibody production and/or secretion can be administered to a subject. Those skilled in the art will understand that any combination of the methods of the invention can be employed.

The present invention can be practiced for medical or veterinary purposes. Suitable mammalian subjects include but are not limited to humans, non-human primates, rats, mice, rabbits, hamsters, cats, dogs, sheep, cattle, pigs, goats and horses. In particular embodiments, the mammalian subject has an autoimmune disease (e.g., SLE) or other condition that is the result of aberrant B cell autoantibody production and/or secretion and/or is at risk for developing an autoimmune disease or other condition that is the result of aberrant B cell autoantibody production and/or secretion. At risk individuals can be identified by family history, genetic analysis or the onset of early symptoms associated with the disease. The mammalian subject can further be an animal model (e.g., a mouse) of autoimmune disease or autoreactive B cell dysfunction (e.g., models of tolerance and loss of tolerance). The mammalian subject is optionally "in need of" the methods of the invention, for example, because the subject is suspected of having or has been diagnosed as having autoimmune disease or is at risk for autoimmune disease or has, is diagnosed with or is at risk for any other condition that results from aberrant autoantibody production and/or secretion by autoreactive B cells.

The cells and compounds (e.g., regulatory cytokines or agents that activate a regulatory immune cell to produce a regulatory cytokine as described above or a nucleic acid encoding either of the foregoing) can be administered to the mammalian subject by any method known in the art, e.g., by intravenous administration, intramuscular delivery or by cellular implant. In particular embodiments, the cells or compounds are delivered by a route that results in delivery to the spleen and/or lymph nodes.

Typically, the cells and compounds will be administered to subjects as a pharmaceutical formulation comprising the cell (s) and/or compound in a pharmaceutically-acceptable carrier. By "pharmaceutically acceptable" it is meant a material that is not biologically or otherwise undesirable, i.e., the material can be administered to a subject without causing any undesirable biological effects such as toxicity.

The pharmaceutical formulation can optionally comprise medicinal agents, pharmaceutical agents, carriers, adjuvants, dispersing agents, diluents, and the like.

The pharmaceutical formulations of the invention can be formulated in accordance with known techniques. See, e.g., Remington, *The Science And Practice of Pharmacy* (latest edition). In the manufacture of a pharmaceutical formulation, the cell or compound (including the physiologically acceptable salts thereof) is typically admixed with, inter alia, a pharmaceutically acceptable carrier. The carrier can be a solid or a liquid, or both, and is optionally formulated with the compound as a unit-dose formulation, for example, a tablet, which can contain from 0.01 or 0.5% to 95% or 99% by weight of the cell or compound. One or more compounds can be incorporated in the pharmaceutical formulations, which can be prepared by any of the well-known techniques of pharmacy.

To facilitate administration, cells can be made into a pharmaceutical composition and/or made into an implant appropriate for administration in vivo, with appropriate carriers or diluents, which further can be pharmaceutically acceptable. The means of making such a composition or an implant have been described in the art (see, for instance, Remington's Pharmaceutical Sciences, latest edition). Where appropriate, the cell can be formulated into a preparation in semisolid or liquid form, such as a capsule, solution, injection, inhalant or aerosol, in the usual ways for their respective route of administration. Means known in the art can be utilized to prevent or minimize release and absorption of the composition until it reaches the target tissue or organ, or to ensure timed-release of the composition.

In particular embodiments, the cell or compound is administered to the subject in a treatment effective amount, as that term is defined herein. Dosages of pharmaceutically active cells and compounds can be determined by methods known in the art, see, e.g., Remington's Pharmaceutical Sciences, latest edition. The treatment effective dosage of any specific cell or compound will vary somewhat depending on the nature of the cell, compound and subject, and will further depend upon the condition of the subject, severity of disease and the route of delivery.

As a general proposition, a dosage from about 0.1 to about 50 mg/kg of the compound will have therapeutic efficacy, with all weights being calculated based upon the weight of the compound, including the cases where a salt is employed.

With respect to cells, typically about $10^2$ to about $10^5$, $10^6$, $10^7$, $10^8$, $10^9$ or $10^{10}$ cells or higher are administered per dose. In other embodiments, about $10^4$ or $10^5$ to about $10^8$, $10^9$ or $10^{10}$ cells or higher are administered per dose. The dosing schedule can be based on well-established cell-based therapies (see, e.g., Topalian and Rosenberg (1987) *Acta Haematol.* 78 Suppl 1:75-6; U.S. Pat. No. 4,690,915). Further, a continuous infusion strategy can be employed.

The pharmaceutical formulations include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver or to the central nervous system. Also encompassed are pharmaceutical formulations for use as cell implants. The most suitable route in any given case will generally depend on the nature and severity of the condition being treated and on the nature of the particular cell or compound which is being delivered.

In particular embodiments, cells are administered intravenously.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like.

Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. The compound or salt can further be provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt thereof. When a compound or salt thereof is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution of the compound. Suitable formulations comprise citrate or bis\tris buffer (pH 6) or ethanol/water and contain from 0.1 to 0.2M of the compound.

A compound can alternatively be formulated for nasal administration or otherwise administered to the lungs of a subject by any suitable means, but is preferably administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the cell or compound in a local rather than systemic manner, for example, in a depot or sustained-release formulation.

Further, the cell or compound can be provided in the form of a liposomal formulation. The technology for forming liposomal suspensions is well known in the art. The liposomal formulations can be lyophilized to produce a lyophilizate which can be reconstituted with a pharmaceutically acceptable carrier, such as water, to regenerate a liposomal suspension.

The present invention further provides methods of evaluating and/or diagnosing specific defects present in a mammalian subject with autoreactive antibody production or autoimmune disease. In representative methods, a regulatory immune cell (e.g., a DC such as a myeloid DC, or a MΦ, such as a marginal zone MΦ, a red pulp MΦ, and/or a metallophilic MΦ, or any combination of the foregoing) from a subject (e.g., a subject with autoreactive antibody production or autoimmune disease) is activated through a TLR pathway, through CD40 antigen and/or through a TNF receptor (as described herein), production of a soluble factor that represses B cell autoantibody production and/or secretion (as described herein) is detected, wherein a reduction in soluble factor production indicates that the subject has a defect in regulatory cell mediated repression of autoantibody secretion by B cells. In particular embodiments, production of IL-6, CD40L and/or a TNF family member (e.g., TNF-α and/or a lymphotoxin such as lymphotoxin-α and/or LIGHT) is determined.

The regulatory immune cell can be removed from a subject, or obtained from a cell removed from a subject, and activated in vitro. For example, peripheral blood cells comprising blood monocytes or HSC from bone marrow can be removed from a subject and differentiated in vitro into DC. Methods of obtaining DC from cultured blood monocytes are known in the art, e.g., monocytes can be cultured in the presence of GM-CSF and IL-4 for around seven days. Alternatively, the regulatory cell can be activated in vivo and regulatory cytokine production can be determined in vitro or in vivo. Bone marrow derived stem cells (HSC) can be obtained from the subject or from a donor using methods known in the art (e.g., culturing in the presence of GM-CSF and/or M-CSF).

By a "reduction" (or grammatical variants thereof) in regulatory cytokine production is meant a decrease of at least about 20%, 25%, 30%, 40%, 50%, 60%, 70%, 80%, 90%, 85%, 98% or more. The reduction in regulatory cytokine production can be assessed by comparison with any suitable control, e.g., the level of regulatory cytokine production from a regulatory immune cell from a healthy subject (e.g., a subject without autoimmune disease).

The present invention is explained in greater detail in the following non-limiting

EXAMPLES

Example 1

General Materials and Methods

Mice. 2-12H and 2-12/Vκ8 immunoglobulin transgenic (IgTg) mice have been described previously (Borrero and Clarke (2002) *J. Immunol.* 168:13-21). The 2-12/Vκ8 mice were maintained on a Cκ−/− background to limit light chain use to Vκ8 or lambda. MyD88$^{-/-}$ mice were a gift of Dr. J. Serody (University of North Carolina, Chapel Hill, N.C.). TLR4$^{-/-}$ mice (Hoshino et al., (1999), *J. Immunol.* 162:3749-3752), generated by Dr. S. Akria (Osaka University, Japan), were kindly provided by Dr. J. Serody (University of North Carolina, Chapel Hill, N.C.) and Drs. D. Schwartz, J. Hollingsworth, and D. Cook (Duke University, Durham, N.C.). Ars/A1 mice (Benschop et al. (2001) *Immunity.* 14:3343) were kindly provided by Dr. L. Wysocki (National Jewish Medical and Research Center, Denver, Colo.). HEL-Ig (MD4; Goodnow et al. (1988) *Nature* 334:676-682) and HEL-IgxsHEL (MD4xML5 (Goodnow et al. (1988) *Nature* 334:676-682) transgenic mice were kindly provided by Drs. K. Hippen (University of Minnesota, Minneapolis, Minn.) and P. Oliver (National Jewish Medical Center). C57BL/6 (non-Tg) mice were purchased from Jackson Labs (Bar Harbor, Me.). Experimental animals were between 8-16 weeks of age and were kept in an accredited animal facility at the University of North Carolina.

Antibodies and other reagents. Antibody to canine distemper virus was purchased from Biodesign International (Saco, Me.). Neutralizing anti-IL-6, rIL-6 and fluorochrome-labeled antibodies specific for CD19, CD3, CD11b, and CD11c were purchased from BD Biosciences (San Diego, Calif.). Antibodies 2.4G2 (anti-CD16/32), 54.1 (3-83 idiotype) (Nemazee and Burki (1989) *Nature* 337:562-566), 2.12.3 (anti-Sm) (Bloom et al. (1993) *J. Immunol.* 150:1591-1610), and Y2 (anti-Sm) (Bloom et al. (1993) *J. Immunol.* 150:1591-1610) were purified from hybridoma culture supernatant. HO13 (anti-Thy 1.2) and Vκ31T (anti-Sm) (Retter et al. (1995) *J. Immunol.* 155:2248-2257) were used as culture supernatants. Isotype-matched, unrelated antibody controls include: 54.1 for anti-IL-6 (rat IgG), HO13 for Vκ31T (mouse IgM), and anti-canine distemper virus (mouse IgG) for 2.12.3. Lipopolysaccharide (LPS) from *E. coli* O55:B5 was purchased from Sigma-Aldrich (St. Louis, Mo.). All experiments with TLR-4$^{-/-}$ DC used LPS (*E. coli* 0111:B4) purchased from List Biological Laboratories (Campbell, Calif.), re-purified (Manthey et al. (1994) *J. Immunol.* 153:2653-2663; Hirschfeld et al. (2000) *J. Immunol.* 165:618-622), and confirmed to be unable to induce IL-6 secretion by TLR4$^{-/-}$ DCs.

Cell purification. B cells were isolated from spleens of 2-12H, 2-12/Vκ8, HEL-Ig, HEL-IgxsHEL, Ars/A1, and non-Tg mice by negative selection using a B cell enrichment cocktail (StemCell Technologies, Vancouver, Canada) and then passed over a MACs column (Miltenyi Biotech, Auburn, Calif.). B cells purified by this method were 90-93% pure as determined by flow cytometry. T cells, CD11c$^+$ cells, and CD11b$^+$ cells were purified from non-Tg mice by positive selection using anti-CD4 and anti-CD8, anti-CD11c, or anti-CD11b microbeads (Miltenyi Biotech, Auburn, Calif.). T cell preparations were 94-97% pure and CD11c$^+$ preparations were 80-95% pure with lymphocytes comprising the contaminating cells. CD11c$^+$ preparations used in the confocal studies were greater than 90% pure. Cell purity was determined by FACs analysis using antibodies against CD19, CD3, CD11b, CD11c from BD Biosciences (San Diego, Calif.).

LPS stimulation. Splenocytes ($1\times10^5$ B cells) or equivalent numbers of purified B cells (purity determined by flow cytometry) were cultured in the presence or absence of LPS (30 μg/mL) for four days. Each culture was set up in triplicate (200 μL volume) in IMDM supplemented with 1 mM sodium pyruvate, 2 mM L-glutamine, 50 μg/mL gentamicin, 100 u/nL penicillin and streptomycin, $5\times10^{-5}$ M 2-mercaptoethanol, and 10% fetal bovine serum (FBS). CD11c$^+$ cells, bone marrow-derived DCs, rIL-6, DC-conditioned medium (CM) (25% of final volume), or anti-IL-6 was added at the initiation of the cultures. To assess the role of soluble factors in repressing Ig secretion, $1\times10^5$ B cells were plated in the upper chamber of a 24-well transwell plate containing a 0.4 μm filter (Corning Incorporated, Corning, N.Y.). rDCs ($1\times10^4$) were added to either the upper chamber containing the B cells or to the lower chamber. The total volume in each well was 700 μL. LPS (30 μg/mL) was added and supernatants were collected after four days.

Bone marrow-derived dendritic cell and macrophage cultures. A single-cell suspension of bone marrow was prepared from the femurs of C57BL/6 mice or TLR-4$^{-/-}$ mice. Following red blood cell lysis, cells were cultured in GM-CSF (10 ng/mL) and IL-4 (10 ng/mL) for five days. Purity was assessed by flow cytometric analysis using CD11b, CD11c, CD3 and B220 (BD Biosciences). State of maturation was assessed by flow cytometric analysis using antibodies specific for MHC class II, B7.2 and CD8 markers (BD Biosciences). The cultures were 99% CD11c$^+$ and had an immature phenotype (MHC class II and B7.2 low). Macrophages were also grown from bone marrow of C57BL/6 mice as described using 20 ng/mL M-CSF (Peprotech, Rocky Hill, N.J.). Purity was assessed by flow cytometric analysis using CD11b and CD11c. Conditioned medium was made from $1\times10^4$ rDCs cultured for an additional four days in a volume of 200 μL with or without LPS (30 μg/mL). The transwell assays used $1\times10^4$ rDCs in a volume of 700 μL.

Immunization. 2-12H and 2-12/Vκ8 mice were pre-bled 1 day before being immunized with snRNPs (100 μg/mouse) emulsified in Complete Freund's adjuvant (CFA) by an intraperitoneal injection. Total volume injected was 500 μL/mouse. Serum levels of anti-Sm or IgM$^a$/κ were detected on day ten after immunization by ELISA as described herein.

ELISA. Anti-Sm in supernatants and serum was measured according to standard methods using 100 μg Sm protein (Immunovision, Springdale, Ariz.) to coat the plates. IgM$^a$/κ (encoded by 2-12H/Vκ8 or Ars/A1) was measured using rat anti-mouse κ (187.1, BD Biosciences), followed by anti-IgM$^a$-biotin (HB100, Bet-1; American Type Culture Collection, Manassas, Va.) and Streptavidin-AP as described (Borrero and Clarke (2002) *J. Immunol.* 168:13). Purified mouse IgM$^a$/κ (TEPC 183; Sigma-Aldrich) was used as a standard control for both anti-Sm and IgM$^a$/κ ELISAs. Mouse anti-HEL IgM$^a$ in supernatants was measured as described (Goodnow et al. (1989) *Nature* 342:385-391). Mouse anti-HEL IgM$^a$ (clone E1) (Inaoki et al. (1997) *J. Exp. Med.* 186:1923-1931) was used as a standard and was a gift from Dr. T. Tedder (Duke University, Durham, N.C.). Data was plotted as either total IgM$^a$/κ levels or as percent of control. Percent of control was calculated as the percent secretion relative to cultures of LPS-stimulated B cells.

ELISPOT. To quantify IgM$^a$/κ producing cells, splenocytes or B cells were stimulated with LPS as described herein. On day three, cells were used in the ELISPOT assay. Multi-screen-IP plates (Millipore; Billerica, Mass.) were coated overnight at 4° C. with rat anti-κ in phosphate-buffered saline (PBS; 1 μg/mL). Plates were blocked with 1% BSA in PBS for one hour at room temperature or overnight at 4° C. Cells were plated in serial dilution in duplicate. Before addition of cells, the plates were washed with PBS and with 0.05% Tween®-20 in PBS after cells were added. Spots were detected using biotinylated-anti-IgM$^a$ (1:2500) followed by Streptavidin-HRP (1:4000; BD Biosciences). Spots were developed using AEC (3-amino-9-ethyl carbazole; Sigma-Aldrich). Spots were analyzed on an ImmunoSpot® Image Analyzer (Cellular Technology; Cleveland, Ohio).

Proliferation Assay. B cell proliferation was determined by stimulating 1×10$^5$ purified B cells with LPS in the presence or absence of rDCs (5×10$^3$) or rIL-6 (10 ng). The cultures were pulsed with 1 μCi per well $^3$H-thymidine (NEN/Dupont Boston, Mass.) during the last eight hours of a 72-hour incubation. The plates were harvested using a Packard Filtermate™ 196 harvester (Packard Instrument Co, Meriden, Conn.) and 20 μL of Microscint™-20 (Packard Instrument Co.) scintillation fluid was added to each well. The plates were counted using a TopCount Scintillation Microplate Reader (Packard Instrument Co). Data was plotted as percent of control calculated as the percent proliferation relative to cultures of LPS-stimulated B cells.

Fluorescence microscopy. Bone marrow-derived DCs (1×10$^6$) were stained on ice in Hanks' Balanced Salt Solution (HBSS) containing 2% fetal calf serum and 0.2% azide. Cells were preincubated with 2.4G2, washed, and stained with Vκ31T (Sm-specific) or HO13 (species- and isotype-matched, unrelated antibody) culture supernatant followed by Cy3-conjugated donkey anti-mouse IgM μ-chain specific F(ab')$_2$ (Jackson ImmunoResearch). Stained cells were adhered to glass coverslips, fixed with 300 μL PBS/3% paraformaldehyde/3% sucrose, and mounted onto glass slides with FluorSave™ (Calbiochem, La Jolla, Calif.). For trypsinization studies, DCs were treated with 0.25% trypsin solution (Sigma-Aldrich) for 30 minutes at room temperature prior to staining. To stain splenic rDCs, 1×10$^6$ ex vivo cells were preincubated with 2.4G2, washed, and stained with Cy3-conjugated 2.12.3 (Sm-specific) or anti-canine distemper virus (species- and isotype-matched control) and then plated onto poly-D-lysine coated glass coverslips. Cells were processed as indicated herein. All samples were viewed on a Zeiss Axioplan 2 imaging microscope using digital deconvolution. Images were renormalized, deconvolved, and rendered in Slidebook™ 3.0 from Intelligent Imaging Innovations, Inc (Denver, Colo.). The deconvolved Cy3 image was rendered into a two-dimensional projection image and overlaid onto a flat nomarski image.

Example 2

Anti-Sm B Cell Anergy

Sm-specific B cells from 2-12/Vk8 immunoglobulin transgenic mice are tolerized by peripheral anergy. Previous studies of tolerance to the lupus-associated antigen, Sm, utilized two immunoglobulin transgenic (IgTg) mouse models. The 2-12H IgTg mouse expresses an unmutated V$_H$J558 gene from the MRL/lpr anti-Sm hybridoma, 2-12 (Bloom (1993) *J. Immunology* 150:1591). Pairing of the 2-12 heavy chain transgene (IgM$^a$ allotype) with endogenous light chains forms a restricted repertoire of Sm-specific B cells (30% of peripheral B cells) and non-autoreactive B cells. Immunization of the 2-12H mice with murine snRNPs elicits an anti-Sm response indicating that some anti-Sm B cells remain functional despite the continued presence of self-antigen (Santulli-Marotto (1998) *Immunity* 8:209). The second model paired the 2-12 heavy chain with a Vκ8 light chain (2-12/Vκ8). This model produces Sm-specific B cells that populate peripheral lymphoid organs, exhibit a prototypic B2 phenotype yet fail to respond to LPS stimulation indicating that tolerance to Sm is maintained by peripheral anergy.

Figure 1:
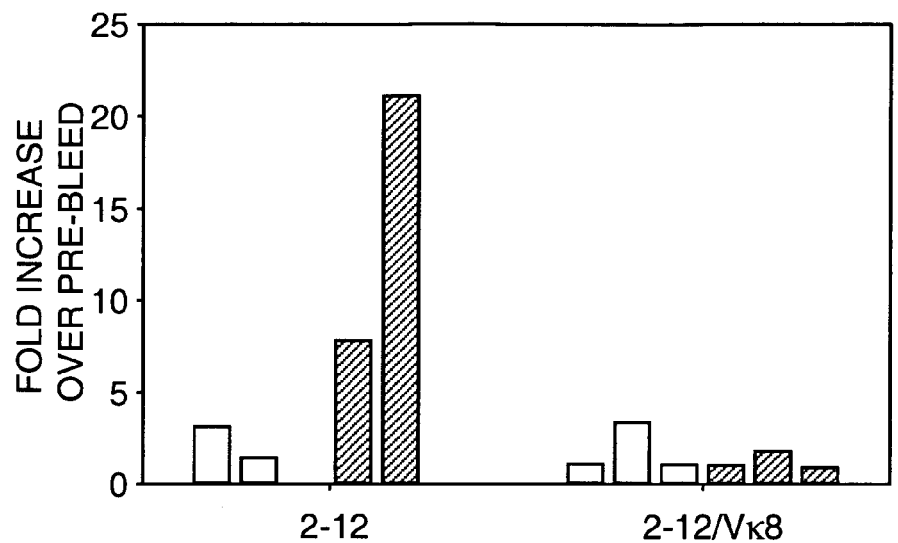
FIG. 1 shows that 2-12/V$\kappa$8 mice are unresponsive to antigen immunization. 2-12H and 2-12/V$\kappa$8 mice were immunized with 100 µg snRNPs emulsified in Complete Freund's adjuvant. Ten days later, serum was collected and anti-Sm or IgM$^a$/$\kappa$ secretion was measured by ELISA. The data are plotted as fold increase over pre-immune serum. Each bar represents an individual mouse.

To assess if the Sm-specific B cell antigen receptor (BCR) was functionally inactive 2-12H (control) and 2-12/Vκ8 mice were immunized with murine snRNPs. As shown in FIG. 1, the 2-12/Vκ8 B cells failed to secrete IgM$^a$/κ in response to snRNP antigen, indicating an anergic phenotype. However, a population of Sm-specific B cells within the 2-12H control mice secreted anti-Sm antibodies (20-fold increase) following immunization with snRNPs. These data demonstrate that snRNP antigen is recognized by anti-Sm B cells but fails to induce an immune response in 2-12/Vκ8 mice, consistent with B cell anergy.

Example 3

CD11c+/CD11b+ Cells Repress Anti-Sm B Cells

Figure 2:
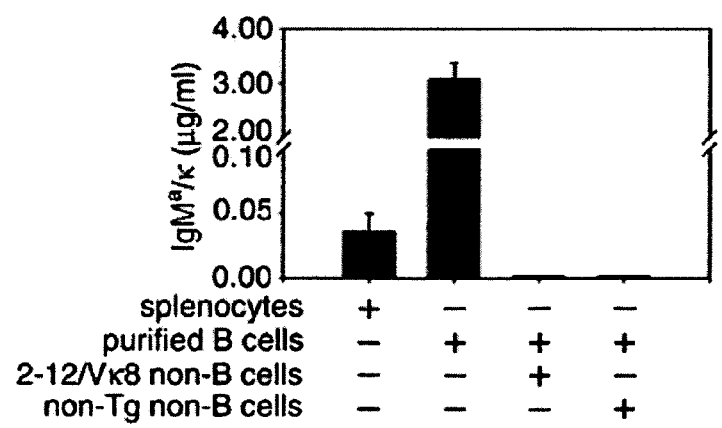
FIG. 2 demonstrates that anergy in 2-12H/V$\kappa$8 cells requires the presence of another cell type. Splenocytes from 2-12H/V$\kappa$8 mice (1×10$^5$ B cells) or equal numbers of purified B cells were cultured alone or with 1×10$^5$ non-B cells from either 2-12H/V$\kappa$8 or non-Tg mice. IgM$^a$/$\kappa$ levels were quantitated by ELISA four days after LPS stimulation.

Tolerance to Sm is reversible and mediated by CD11b$^+$/CD11c$^+$ cells. B cells from mice expressing the 2-12H Ig heavy chain transgene (IgM$^a$) paired with a Vκ8 light chain transgene recognize Sm. Sm-specific B cells are evident in the periphery but are unresponsive to LPS stimulation or antigen immunization suggesting they are regulated by peripheral anergy (Borrero and Clarke, (2002), *J. Immunol.* 168:13-21; FIG. 1). Sm-specific B cells exhibit a normal lifespan, enter the B cell follicle normally, and do not down-modulate IgM. During the characterization of anergic Sm-specific B cells, it was unexpectedly observed that purified B cells secreted IgM$^a$/κ in response to LPS, whereas unpurified splenocytes remained LPS-unresponsive (Borrero and Clarke, (2002), *J. Immunol.* 168:13-21) (FIG. 2). Interestingly, reconstitution of purified Sm-specific B cell cultures with splenocytes depleted of B cells (henceforth called non-B cells) repressed IgM$^a$/κ secretion. Repression was not limited to non-B cells from 2-12H/Vk8 mice as co-culture of Sm-specific B cells with non-B cells from non-Tg mice also inhibited IgM$^a$/κ secretion (FIG. 2). These data show that the unresponsive phenotype of Sm-specific B cells is reversible and conferred by non-B cells.

Figure 3:
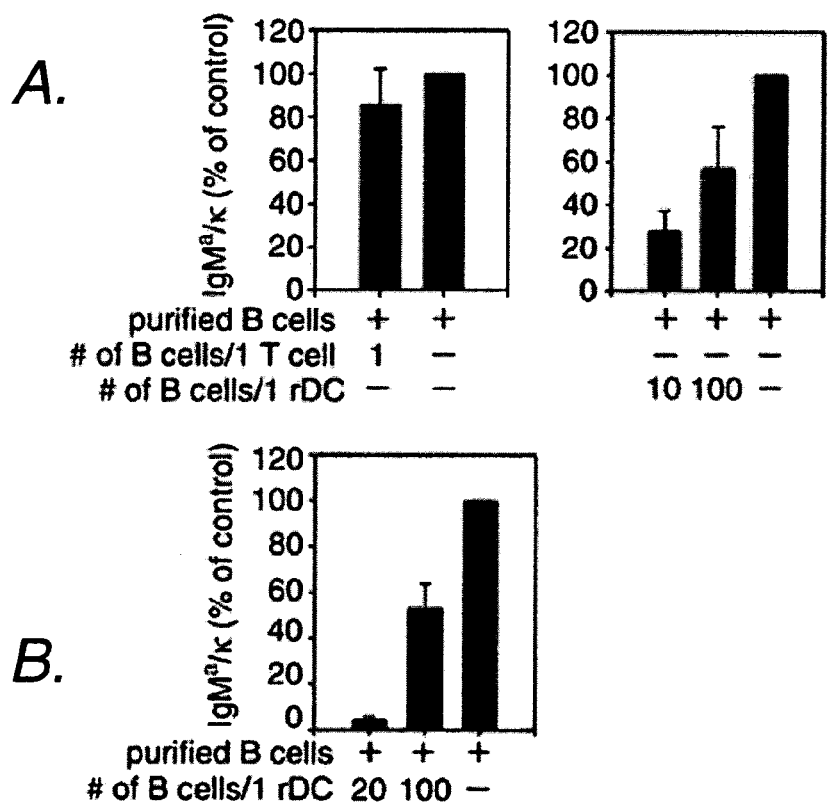
FIG. 3 shows that rDCs prevent Ig secretion by Sm-specific B cells. 1×10$^5$ Sm-specific B cells were cultured with the indicated number of splenic T cells or rDCs (Panel A), or bone marrow-derived rDCs from non-Tg mice (Panel B). Cells were LPS stimulated and IgM$^a$/$\kappa$ was quantitated after four days by ELISA. LPS-stimulated B cells (100%) secreted 2-10 µg/ml. Data represent at least four experiments.

To identify the regulatory cell(s) responsible for Ig repression, purified T cells and DCs were co-cultured with Sm-specific B cells. T cells failed to inhibit LPS-induced-IgM$^a$/κ secretion when cultured at ratios comparable to those found in spleen (FIG. 3, Panel A, left graph). However, ex vivo DCs (CD11b$^+$/CD11c$^+$) repressed 75% of IgM$^a$/κ secretion when one regulatory DC (rDC) was co-cultured with ten B cells (FIG. 3, Panel A, right graph). To confirm that DCs repress Ig secretion, bone marrow-derived DCs (CD11b$^+$/CD11c$^+$) were co-cultured with Sm-specific B cells. As shown in FIG. 3, Panel B, bone marrow-derived DCs repressed LPS-induced IgM$^a$/κ secretion in a dose-dependent manner. Maximal repression was observed when one rDC was co-cultured with twenty B cells. These results show that rDCs are capable of maintaining autoreactive B cells in an unresponsive state.

Figure 4:
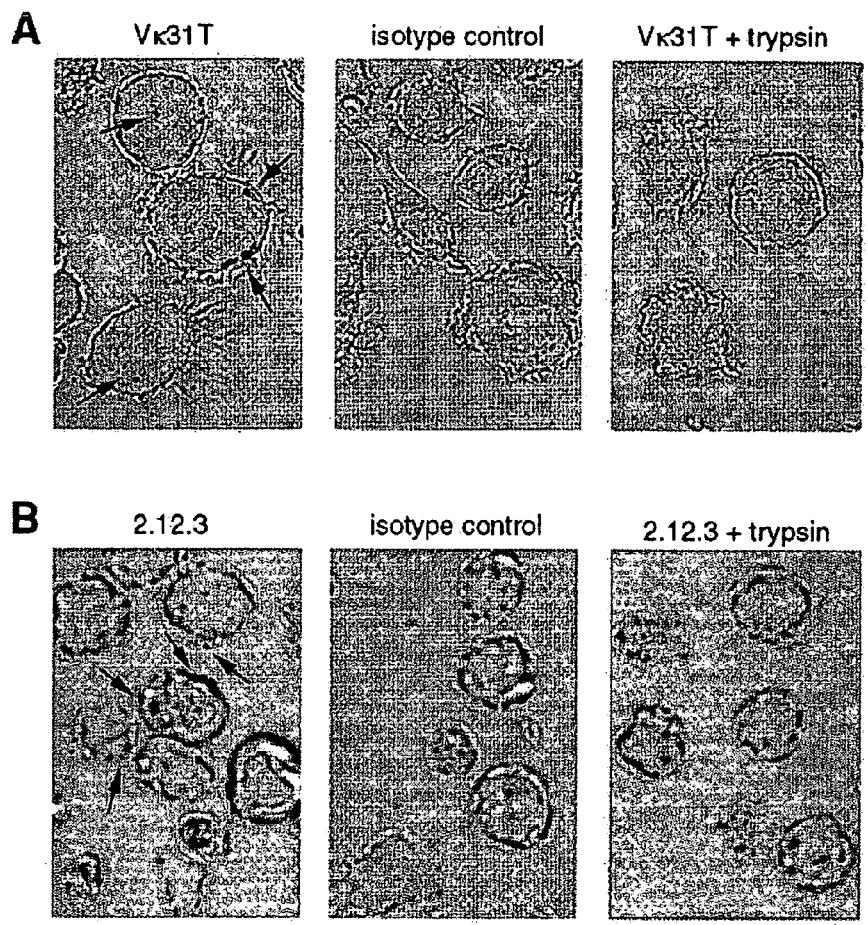
FIG. 4 shows that rDCs express surface Sm. Bone marrow-derived DCs (99% CD11c$^+$) (Panel A) or ex vivo splenic rDCs (≥90% CD11c$^+$) (Panel B) were stained with anti-Sm (Vκ31T or 2.12.3, left and right images) or with a species- and isotype-matched, unrelated antibody (middle images). DCs were either treated with trypsin (right images) or left untreated (left and middle images). Arrows denote Sm staining.

Further characterization showed that a large percentage of the CD11c$^+$/CD11b$^+$ positive cells also co-express DX5 (data not shown).

rDCs display Sm antigens on their cell surface. Since all previously described models of B cell tolerance require self-antigen, it was determined whether rDCs provide a source of self-antigen to autoreactive B cells. It is known that DCs take up antigens and induce T-independent antigen-specific humoral immune response (Balazs et al. (2002) *Immunity* 17:341-352). To assess if rDCs display nuclear self-antigens such as Sm, these cells were analyzed using fluorescence microscopy. Non-permeabilized bone marrow-derived rDCs display punctate, Sm-specific staining (FIG. 4, Panel A). Ex vivo splenic rDCs displayed a similar staining pattern when stained with an independently-derived Sm-specific antibody (FIG. 4, Panel B). Quantitation of three independent experiments revealed that 46% of bone marrow-derived rDCs and 54% of ex vivo rDCs exhibited Sm-specific staining. This staining was evident with a third independently-derived Sm-specific antibody (not shown) and was specific, since isotype-matched, unrelated antibodies failed to stain (FIG. 4, Panels A and B) (Retter et al. (1995) *J. Immunol.* 155:2248-2257; Bloom et al. (1993) *J. Immunol.* 150:1591-1610). Staining was not due to passive antibody internalization, since trypsin-treated rDCs failed to stain (FIG. 4, Panels A and B). These data show that rDCs display nuclear self-antigen on their surface coincident with their ability to regulate autoreactive B cells.

Example 4

Signaling Through Surface B Cell Antigen Receptors

Apoptotic cells maintain unresponsiveness but also activate under specific conditions. Apoptosis is an active cell death process that avoids the release of intracellular contents. Efficient clearance of these cells by phagocytes is very important in regulating inflammation and autoimmune disease. Apoptotic cells display nuclear antigens on their cell surface (data not shown). To determine if continued presence of antigen displayed on apoptotic cells could maintain repression of anti-Sm B cells in the absence of dendritic cells, B cells were purified into collection tubes containing apoptotic cells. B cells added to apoptotic cells immediately after purification remained repressed, indicating that continued signaling through the BCR maintains the unresponsive state (data not shown). However, apoptotic cells added to B cells 30 minutes after purification failed to repress autoantibody secretion. Unexpectedly, it was found that addition of apoptotic cells to purified 2-12/Vκ8 B cells 30 minutes after purification not only failed to repress autoantibody secretion but enhanced secretion of IgM$^a$/κ 2-fold. (data not shown). To address whether this stimulatory effect resulted in renewed signal transduction through the BCR, 2-12/Vκ8 B cells were purified and stimulated with either snRNPs or apoptotic cells. snRNPs did not renew signal transduction by purified 2-12N/Vκ8 B cells but apoptotic cells induced renewed tyrosine phosphorylation (data not shown). However, the snRNPs were capable of stimulating 2-12 B cells consistent with a sub-population within the 2-12H mouse maintaining a naïve phenotype. These data are consistent with apoptotic cells stimulating B cells that fail to engage Sm on the surface of dendritic cells.

Figure 5:
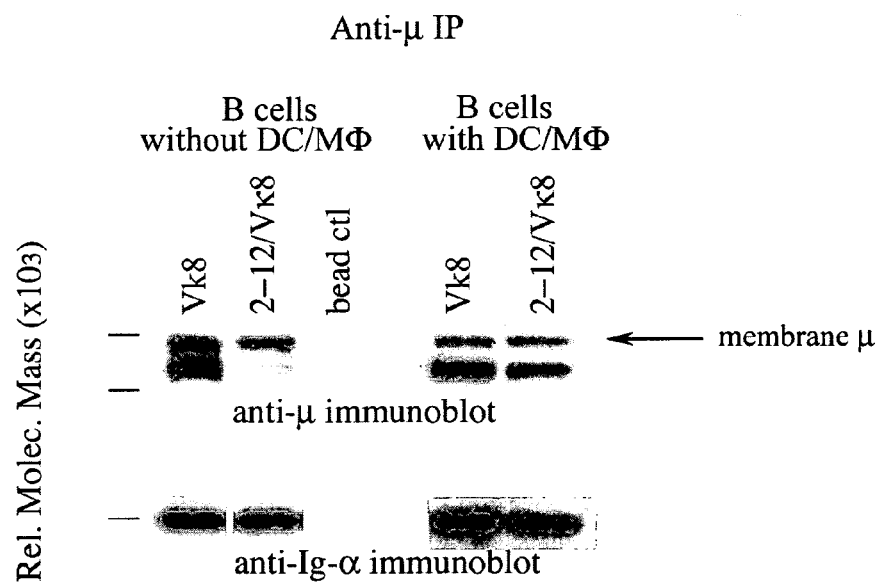
FIG. 5 shows that in the presence of DC/MΦ, the Ig-α signal-transducing subunit of the B cell antigen receptor (BCR) is uncoupled from IgM. Whole cell lysates were made from 2-12/Vκ8 or naïve Vκ8 B cells either alone (left panel) or in the presence of DC/MΦ (10-15%) (right panel) and IgM was immunoprecipitated and analyzed by SDS-PAGE. The anti-μ immunoprecipitates were then immunoblotted with anti-μ and anti-Ig-α. To compare IgM associated Ig-α levels between anergic and naïve cells, lanes with equal loading of IgM were compared.

2-12/Vκ8 B cells exhibit destabilized receptors in the presence of rDC/MΦ. To assess if the presence of Sm protein on the surface of apoptotic cells was functional in BCR-mediated responses, it was determined whether BCR-mediated signal transduction had occurred by B cells engaged with dendritic cells. It has been shown that signal transduction through the BCR destabilizes the antigen-bound μ-heavy chain from the Ig-α/β signal transduction complex. Receptor destabilization requires BCR-mediated kinase activation and results in surface immunoglobulin capable of binding antigen but unable to transduce signals. The destabilized receptors inhibit renewed signal transduction of naïve, coupled receptors. It was contemplated that if Sm expression by the rDC/MΦ population activated BCR-mediated signal transduction, BCR destabilization might be evident. As shown in FIG. 5, right panel, 2-12/Vκ8 B cells containing 15-20% CD11b$^+$/CD11c$^+$ cells exhibit a reduced association of Ig-α/β in anti-μ immunoprecipitates compared to Vκ8 transgenic B cells FIG. 5, right panel, lane 1 compared to lane 2, Ig-α immunoblot). This was not simply due to unequal immunoprecipitation since the levels of membrane μ were comparable (FIG. 5, right panel, anti-μ immunoblot). Unexpectedly, it was found that B cells purified to >93% homogeneity exhibited comparable levels of Ig-α/β associated with μ-heavy chain, indicating that re-association of the receptor complex occurs in the absence of the rDC/MΦ population (FIG. 5, right panel, lane 1 compared to lane 2). These data indicate that destabilization of the BCR may play a role in maintaining the unresponsive phenotype in the absence of TLR ligation.

Example 5

IL-6 Represses Ig Secretion

Figure 6:
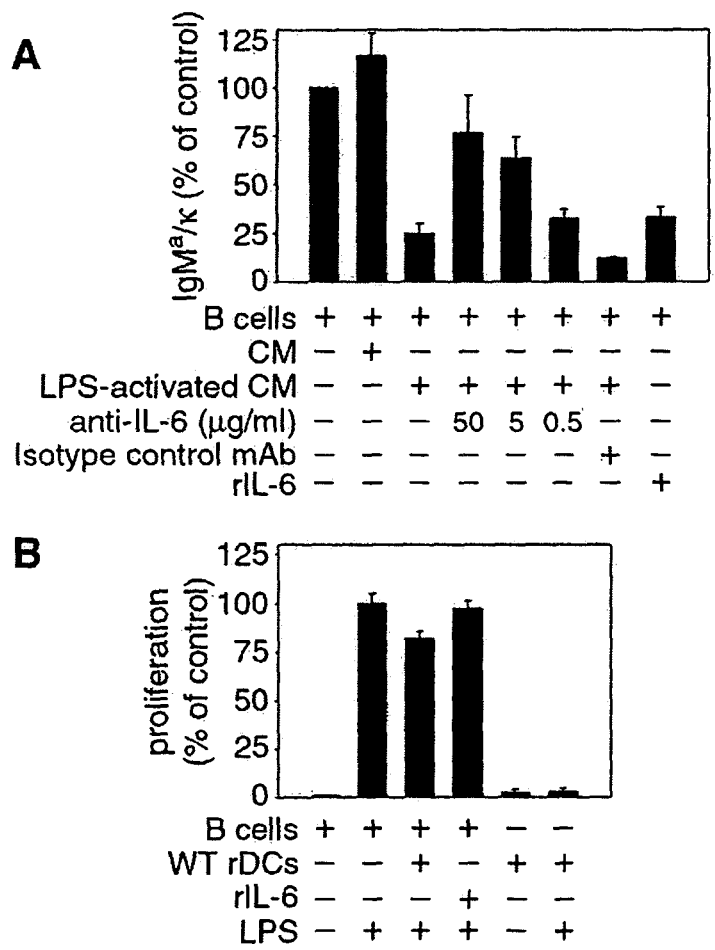
FIG. 6 shows that a rDC-derived, soluble factor maintains anergy of Sm-specific B cells. Panel A, Sm-specific B cells (1×10$^5$) were stimulated with LPS (30 μg/mL) in the presence of either rDC conditioned medium (CM) or LPS-activated rDC-CM, anti-IL-6, isotype-matched control mAb (50 μg/mL) or rIL-6 (10 ng/mL). IgM$^a$/κ secretion was quantitated by ELISA. LPS-stimulated B cells (100%) from three experiments secreted 2-10 μg/mL of IgM$^a$/κ. Panel B, Unstimulated or LPS-stimulated Sm-specific B cells (1×10$^5$) were cultured with rDCs (5×10$^3$) or rIL-6 (10 ng/mL). Proliferation was determined on day two by $^3$H-thymidine incorporation. The data from four experiments is plotted as percent proliferation relative to LPS-stimulated B cells (CPM range=75000-130000).

Secretion of IL-6 by activated rDCs represses Ig secretion. The low numbers of rDCs required to repress Ig secretion suggested that a soluble factor was responsible. To test this, we co-cultured Sm-specific B cells with conditioned medium (CM) from unstimulated and LPS-stimulated rDCs. LPS-stimulated rDC-CM, but not unstimulated rDC-CM, inhibited 75% of IgM$^a$/κ secretion suggesting that a soluble factor secreted by rDCs repressed Ig secretion (FIG. 6, Panel A). To identify the soluble factor responsible, we neutralized LPS-stimulated CM with antibodies specific for 13 different cytokines as well as pertussis toxin to block chemokine receptors (data not shown). Neutralization of IL-6 restored IgM$^a$/κ secretion to 75% of control while an unrelated antibody failed to relieve repression (FIG. 6, Panel A). To confirm that IL-6 was sufficient, rIL-6 was tested for its ability to repress Ig secretion. rIL-6 repressed IgM$^a$/κ secretion albeit slightly less efficiently than LPS-stimulated CM (FIG. 6, Panel A). To rule out the possibility that repression simply reflected lack of proliferation, or was due to cell death, we monitored trypan blue exclusion and measured the incorporation rate of thymidine by purified B cells stimulated with LPS, in the presence and absence of rDCs or rIL-6. B cells co-cultured with or without rDCs, or IL-6, showed comparable proliferation (FIG. 6, Panel B). Viability within all cultures was comparable (data not shown) indicating that rDC-mediated repression of Ig secretion is not a reflection of cell death or changes in B cell proliferation. These data show that Ig secretion by autoreactive B cells is regulated by cytokines, representing the first evidence that IL-6 represses Ig secretion.

Example 6

Cell-Cell Contact Induces Partial Repression of Ig Secretion

Figure 7:
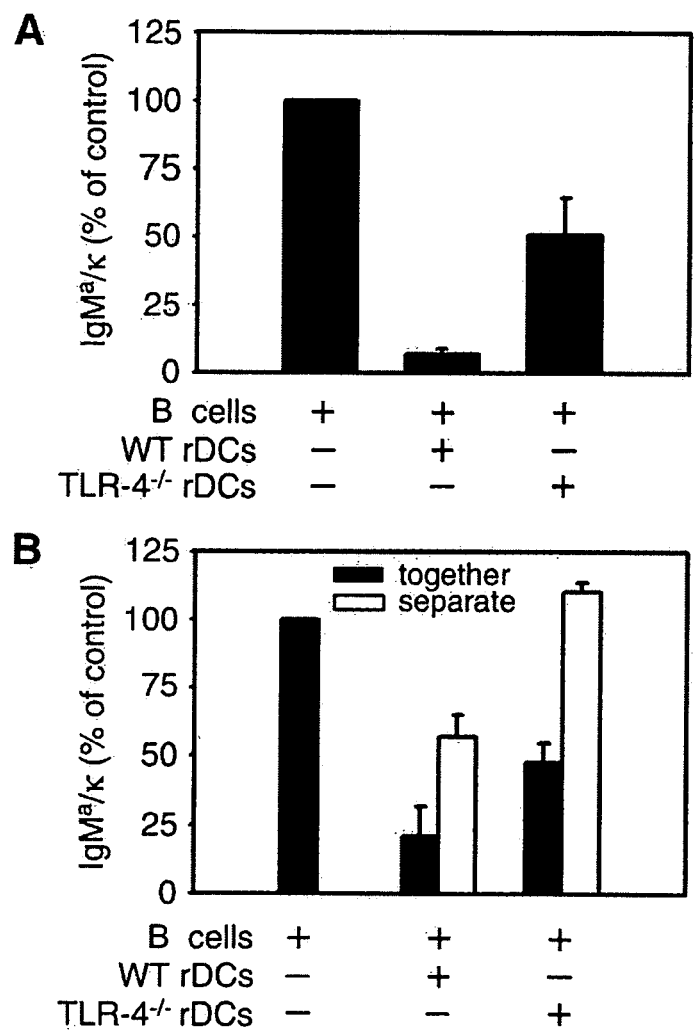
FIG. 7 shows that rDCs partially tolerize Sm-specific B cells by a contact-dependent mechanism. Panel A, 1×10$^5$ Sm-specific B cells were LPS-stimulated (30 μg/mL) in cultures with or without 5×10$^3$ bone marrow-derived wild-type or TLR-4$^{-/-}$ rDCs. IgM$^a$/κ was quantitated at day four. Data represent four experiments. Panel B, B cells (1×10$^5$) and bone marrow-derived rDCs (1×10$^4$) were cultured together or separately under conditions described in (Panel A) using a transwell system containing a 0.4 μm permeable membrane. Data represent two to five experiments.

Interaction between rDC and Sm-specific B cells is required for optimal rDC-mediated repression. Collectively, the data show that LPS-stimulated dendritic cells secrete a factor that is capable of repressing autoantibody secretion. Repression of autoantibody secretion requires that the B cell has prior antigen experience. It was contemplated that expression of Sm antigen on the dendritic cell surface might serve two purposes. The first would be to continually engage surface B cell antigen receptors (BCR) such that the receptors remain desensitized to renewed signal transduction. The second function may be to bring the B cell in close proximity to the dendritic cell such that secondary stimulation by pattern recognition receptors such as TLR4 would allow the local concentration of the soluble mediators to further repress the B cell. To determine whether rDCs contribute to B cell unresponsiveness in the absence of cytokine production, the ability of Sm-specific B cells to secrete IgM$^a$/κ when co-cultured with TLR-4 deficient rDCs was assessed. Unexpectedly, TLR-4$^{-/-}$ rDCs repressed 50% of LPS-induced IgM$^a$/κ secretion by Sm-specific B cells, compared to 93% repression by wild-type rDCs (FIG. 7, Panel A). To further define the IL-6-independent mechanism by which rDCs repress Ig secretion, Sm-specific B cells were cultured with either wild-type rDCs or TLR-4$^{-/-}$ rDCs in a transwell apparatus. Co-culture of B cells and wild-type rDCs maintained cell-cell contact and permitted IL-6 diffusion. This repressed IgM$^a$/κ secretion to 20% of the control (FIG. 7, Panel B). In contrast, separation of B cells and wild-type rDCs during culture abolished cell-cell contact but permitted IL-6 diffusion. This repressed Ig secretion to approximately 60% of control indicating that both IL-6 and cell-cell contact contributed to repressing Ig secretion. When Sm-specific B cells were co-cultured with TLR-4$^{-/-}$ rDCs, cell-cell contact was maintained in the absence of IL-6 production and secretion of IgM$^a$/κ was reduced to 50% of the control. Unexpectedly, physical separation of TLR-4$^{-/-}$ rDCs from Sm-specific B cells, which abolished cell-cell contact and IL-6, failed to repress IgM$^a$/κ, confirming that cell-cell contact induces partial repression. (FIG. 7, Panel B). These findings show that rDCs suppress Ig secretion by providing IL-6 and by a contact-dependent mechanism.

Example 7

IL-6 Repression of Chronically Antigen-Experienced B Cells

Figure 8:
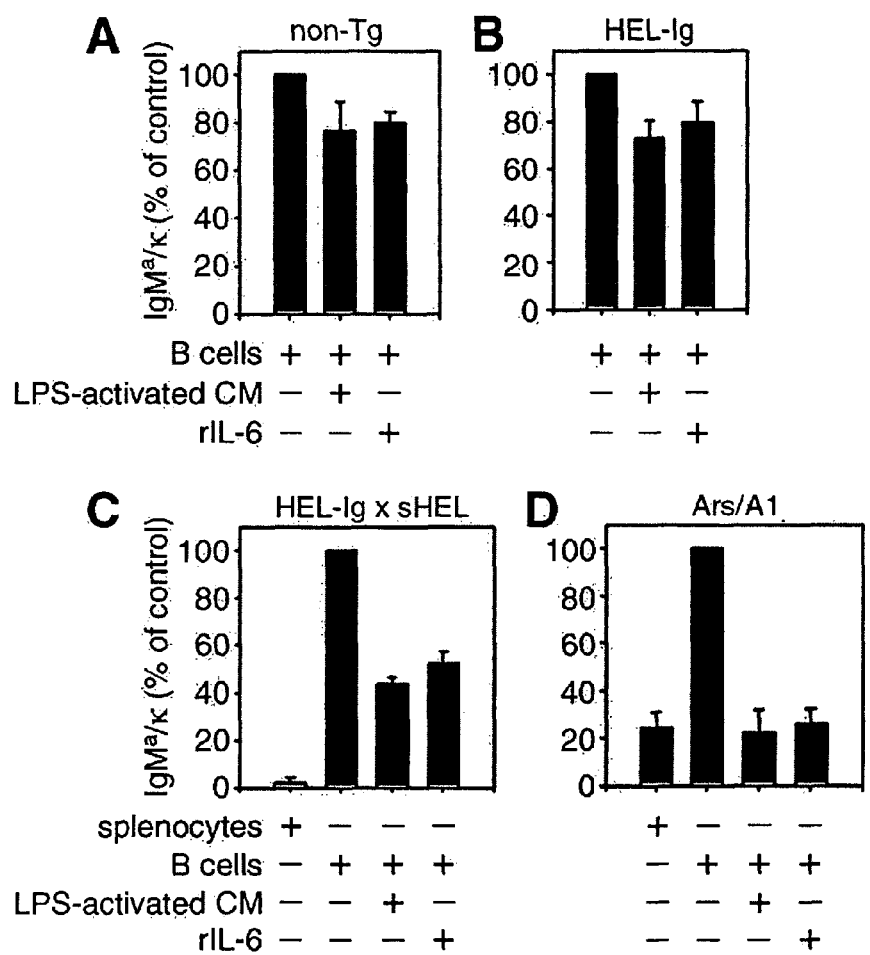
FIG. 8 Chronically antigen-experienced, but not naïve, B cells are susceptible to repression by IL-6. 1×10$^5$ non-Tg (Panel A), HEL-Ig (Panel B), HEL-Ig×sHEL (Panel C), or Ars/A1 B cells (Panel D), either purified or unpurified, were stimulated with LPS (30 μg/mL) alone or in the presence of LPS-activated rDC-derived CM or rIL-6 (10 ng/mL) for four days. IgM$^b$, anti-HEL IgM$^a$, and IgM$^a$/κ were quantitated by ELISA. From four experiments, LPS-stimulated B cells (100%) secreted 14-42 μg/mL (Panel A), 7-27 μg/mL (Panel B), 8-32 μg/mL (Panel C) and 2-5 μg/mL (Panel D) of Ig.

IL-6 promotes differentiation (Muraguchi et al. (1988) *J. Exp. Med.* 167:332-344) and long-term survival (Minges Wols et al. (2002) *J. Immunol.* 169:4213-4221) of plasma cells and renders responder T cells refractory to T$_{reg}$ suppression (Pasare and Medzhitov (2003) *Science* 299:1033-1036). The results demonstrating that IL-6 represses Ig secretion by Sm-specific B cells under conditions reported to promote polyclonal lymphocyte activation were therefore unexpected. It was contemplated that chronic antigen exposure might alter the response of B cells to IL-6. Accordingly, the effects of IL-6 on non-Tg (naïve) B cells and chronically antigen-experienced B cells were compared. As shown in FIG. 8, Panel A, B cells from non-Tg mice secreted Ig in response to LPS and were unaffected by co-culture with CM from LPS-stimulated rDCs or rIL-6. Similarly, LPS-induced Ig secretion by naïve HEL-specific B cells (HEL-Ig) was comparable in the presence or absence of IL-6 (FIG. 8, Panel B). However, chronically antigen-experienced HEL-specific B cells (HEL-Ig× sHEL) showed a 57% reduction in secreted Ig under the same conditions (FIG. 8, Panel C). These data show that IL-6 represses Ig secretion by B cells continuously exposed to self-antigen.

To determine whether rDC-mediated repression affects B cells specific for other lupus-related antigens, B cells from Ars/A1 IgTg mice (FIG. 8, Panel D) were analyzed. B cells from these mice bind the hapten p-azophenylarsonate (Ars) and ssDNA (Benschop et al. (2001) *Immunity* 14:3343). Unpurified Ars-specific B cells failed to secrete Ig upon LPS stimulation, consistent with an anergic state. However, purification of Ars-specific B cells reversed their unresponsive state permitting IgM$^a$/κ secretion (FIG. 8, Panel D). Addition of rIL-6 or CM from LPS-stimulated rDCs repressed 74% of Ig secretion. These results demonstrate that Ig secretion by autoreactive B cells is regulated by IL-6 and self-antigen.

Figure 9:
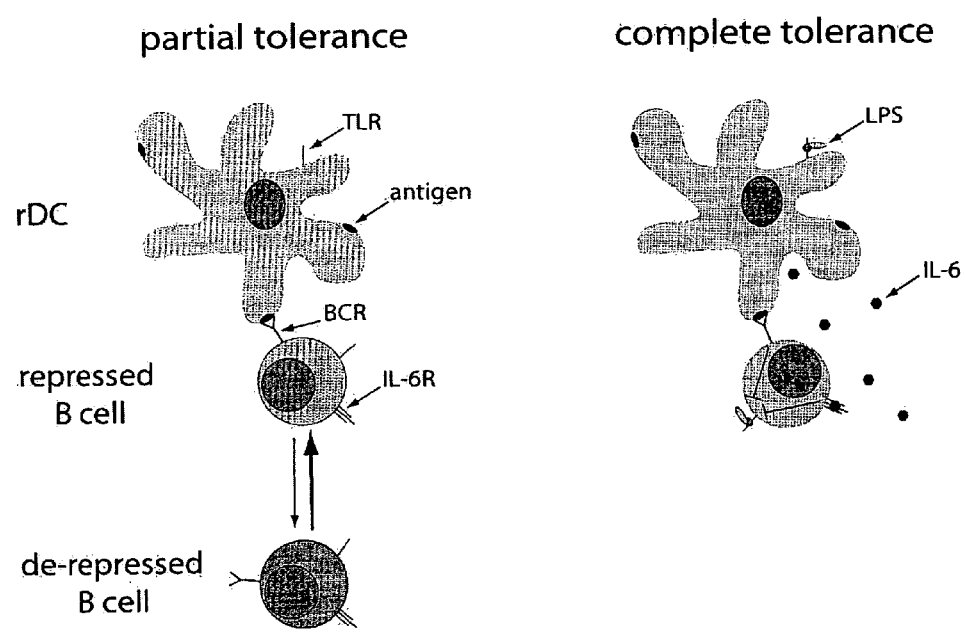
FIG. 9 presents a model in which rDCs maintain B cell tolerance by a dual mechanism. Contact between rDC and autoreactive B cells induces a state of partial tolerance. This likely represents antigen/BCR engagement as depicted in the left panel (repressed B cell). These cells secrete 50% less Ig compared to B cells that fail to engage rDCs (de-repressed B cells). Under conditions of polyclonal activation, repression mediated by cell-cell contact is insufficient to maintain tolerance of autoreactive B cells. Complete tolerance is provided by IL-6 and cell-cell contact as depicted in the right panel. These conditions inhibit 95% of Ig secretion.

Not to be bound by theory, the data collectively indicate that since only chronically antigen-experienced B cells are susceptible to repression by rDCs, that Sm antigen displayed on surface of rDCs engages the BCR to regulate autoreactive B cells in the absence of polyclonal activation (FIG. 9, left panel). A second level of regulation is required under conditions of polyclonal activation. This is provided by activated rDCs that secrete IL-6. (FIG. 9, right panel). IL-6 (and other regulatory cytokines), combined with chronic antigen/BCR stimulation, represses LPS-induced Ig secretion to approximately 80% of the control and only B cells chronically exposed to self-antigen are susceptible to IL-6-mediated repression. The importance of this mechanism is underscored by the identification of IL-6 as a polyclonal activator of T cells (Pasare et al. (2003) *Science* 299:1033-1036), wherein activated dendritic cells were found to promote polyclonal activation of CD4$^+$ T$_h$ cells by blocking T$_{reg}$-mediated suppression. Thus, under conditions of bacterial or viral infection, stimulation by pathogen-associated molecular patterns (PAMPS) induces dendritic cells to secrete cytokines that polyclonally activate naïve B and T cells while simultaneously repressing autoreactive B cells thereby promoting immunity while preventing autoimmunity. This illustrates how B cell tolerance and immunity are balanced during polyclonal activation.

Example 8

LPS-Activated DCs Secrete TNFα to Regulate Ig Secretion by Autoreactive B Cells

Figure 10:
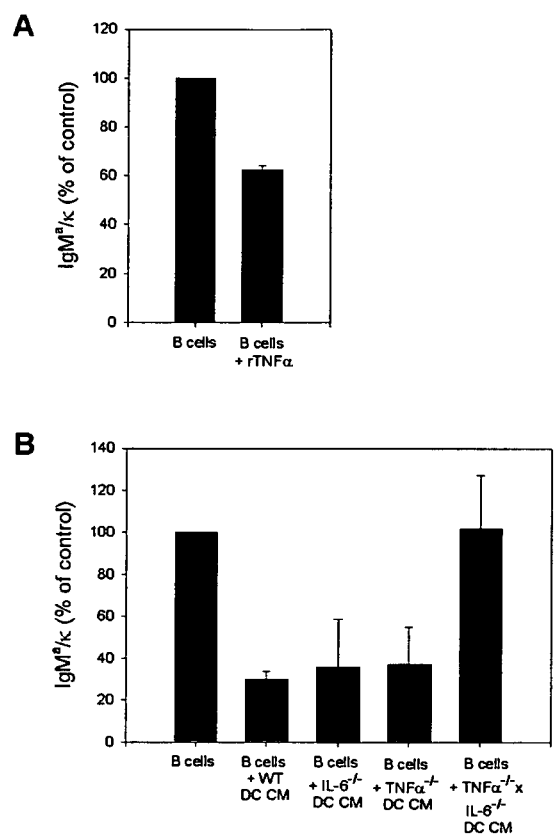
FIG. 10 shows that TNFα represses Ig secretion by Sm-specific B cells. Sm-specific B cells (1×10$^5$) were stimulated with LPS (30 μg/ml) in the presence of rTNFα (50 ng/ml) (A), or WT DC CM, IL-6$^{-/-}$ DC CM, TNFα$^{-/-}$ DC CM, or IL-6$^{-/-}$×TNFα$^{-/-}$ DC CM (B). IgM$^a$/κ was quantitated by ELISA on day 4. Data is representative of two experiments.

DCs and MΦs regulate autoreactive B cells during innate immune responses. In the case of DCs, activation of the innate immune response induces IL-6 production. IL-6 selectively acts on B cells chronically exposed to self-antigen to repress Ig secretion. To assess if additional soluble mediators repressed Ig secretion, conditioned medium (CM) was prepared from IL-6-deficient DCs and tested if it regulated Sm-specific B cells. As shown in FIG. 10 (panel B), CM prepared from IL-6-deficient DCs repressed 60% of Ig secretion comparable to the level of repression seen when CM from wild-type (WT) DCs was cultured with autoreactive B cells. This indicates that in addition to IL-6, other soluble factors repress Ig secretion by autoreactive B cells. To identify the other factor(s), IL-6$^{-/-}$ DC CM was neutralized with antibodies to a number of cytokines, chemokines and soluble mediators. Polyclonal antibodies to TNF-α neutralized the repressive effect; however, insufficient polyclonal antisera were available to reproduce the finding. To further investigate the possibility that TNFα repressed Ig secretion, recombinant TNFα was added to LPS-stimulated B cells and Ig secretion measured. As shown in FIG. 10 (panel A), recombinant TNFα repressed 43% of Ig secretion. If IL-6 and TNFα were the only soluble mediators that repressed autoantibody production, it seemed that DCs derived from IL-6$^{-/-}$×TNFα$^{-/-}$ mice would fail to repress. LPS-activated CM from DCs derived from the bone marrow of mice deficient in both cytokines was tested for its ability to repress. As shown in FIG. 10 (panel B), DCs derived from IL-6$^{-/-}$ or TNF$^{-/-}$ DCs repressed 60% of Ig secretion; however, deficiency in both cytokines relieved repression and autoantibody secretion was restored to control levels. These data establish that in addition to IL-6, LPS-activated DCs secrete TNFα to regulate Ig secretion by autoreactive B cells.

Example 9

Materials and Methods

Secretion of CD40 Ligand and IL-6 by MΦs represses Ig Secretion by Autoreactive B Cells Mice 2-12/Vκ8 immunoglobulin transgenic (IgTg) mice were maintained on a Cκ$^{-/-}$ background and have been previously described (Borrero et al., (2002) *J. Immunol*. 168:13-21). The Ars/A1 IgTg mice were previously described (Benschop et al., (2001) *Immunity* 14:3343). HEL-Ig (MD4) and HEL-Ig× sHEL (MD4×ML5) (Goodnow et al., (1988) *Nature* 334:676-682) transgenic mice, C57BL/6 (non-Tg), IL-6$^{-/-}$, CD40L$^{-/-}$, and MRL/lpr mice were purchased from Jackson Labs (Bar Harbor, Me.). Experimental animals were between 8-16 weeks of age and maintained in an accredited animal facility at the University of North Carolina or at National Jewish Medical and Research Center, Denver, Colo.

Antibodies and Other Reagents

Neutralizing anti-CD40L, hamster IgG (isotype control for anti-sCD40L), neutralizing anti-IL-6, anti-IL-6-biotin, and rIL-6 were purchased from BD Biosciences (San Diego, Calif.). Recombinant CD40L was purchased from R&D Systems (Minneapolis, Minn.). 187.1 (anti-κ), HB100 (anti-IgM$^a$), 33-60 (anti-IgM), and B7.6 (anti-IgM) were purified from hybridoma culture supernatant. M-CSF was purchased from Peprotech (Rocky Hill, N.J.) and LPS from *E. coli* 055:B5 was purchased from Sigma-Aldrich (St. Louis, Mo.).

Cell Purification

B cells were isolated from spleens of 2-12H/Vκ8, HEL-Ig, HEL-Ig×sHEL, Ars/A1, and non-Tg mice by negative selection (StemCell Technologies, Vancouver, Canada). B cells were 83-93% pure as determined by flow cytometry. MΦ (CD11b$^+$) were purified from non-Tg mice by positive selection using anti-CD11b microbeads (Miltenyi Biotec, Auburn, Calif.). Ex vivo MΦ preparations were 70% pure with the contaminating cells comprising 10% DCs and 20% lymphocytes.

Bone Marrow-Derived MΦ Cultures

Single-cell suspensions of murine bone marrow were prepared from the femurs of non-Tg mice. Following red blood cell lysis, cells were cultured in M-CSF (20 ng/ml) for seven days. MΦ cultures were 98% CD11b$^+$. Phenotypically, the cultures were I-A$^{neg}$ and B7.2$^{neg}$. Conditioned medium (CM) was made from 1×10$^4$ MΦ cultured for an additional four days in the presence or absence of LPS (30 μg/ml).

LPS Stimulation

Splenocytes (1×10$^5$s B cells), or equivalent numbers of purified B cells, (purity determined by flow cytometry) were cultured in triplicate in IMDM supplemented with 1 mM sodium pyruvate, 2 mM L-glutamine, 50 μg/ml gentamicin, 100 u/ml penicillin and streptomycin, 5×10$^{-5}$ M 2-mercaptoethanol, and 10% FBS in the presence of LPS (30 μg/ml) for four days. CD11b$^+$/CD11c$^+$ splenocytes, bone marrow-derived MΦs, recombinant sCD40L, MΦ CM (25% of final volume), or anti-CD40L were added at day 0.

ELISAs

IgM$^a$/κ (encoded by 2-12H/Vκ8 or Ars/A1) was measured using rat anti-mouse κ (187.1), followed by biotin-labeled anti-IgM$^a$ (HB100, Bet-1; American Type Culture Collection, Manassas, Va.) and Streptavidin-AP as described (Borrero et al., (2002) *Immunol*. 168:13-21). Purified mouse IgM$^a$/κ (TEPC 183; Sigma-Aldrich) was used as a standard control for both anti-Sm and IgM$^a$/κ ELISAs. IgM (non-Tg) was detected using anti-mouse IgM (clone 33-60) and biotin-labeled anti-mouse IgM (B7.6). Mouse anti-HEL IgM$^a$ in supernatants was measured as described (7). Mouse anti-HEL IgM$^a$ (clone E1) (Inaoki et al., (1997) *J. Exp. Med*. 186:1923-1931) was used to generate a standard curve and was a gift from Dr. T. Tedder (Duke University, Durham, N.C.). IL-6 was measured using anti-IL-6 and biotin-labeled anti-IL-6 according to the manufacture's directions (BD Biosciences). Data were plotted as percent of control calculated as the percent secretion relative to purified cultures of LPS-stimulated B cells. Alternatively, the levels of IgM$^a$/κ, IL-6, or sCD40L were plotted relative to a standard curve of recombinant protein or purified IgM.

ELISPOT

The number of antibody secreting cells (ASCs), was determined as previously described (Qian et al., 2004) *J. Immunol*. 172:625-635). Briefly, LPS-stimulated B cells, cultured in the presence or absence of recombinant sC40L for three days, were added to Multiscreen-IP plates (Millipore, Billerica, Mass.) that were coated with 10 U/well Sm Ag (Immunovision, Springdale, Ariz.). The cells were incubated for eight hours at 37° C. The ASC were detected using biotin-labeled anti-IgM$^a$ followed by streptavidin-HRP (BD Biosciences) and 3-amino-9-ethylcarbazole (Sigma) in 0.1M acetate buffer. The plates were analyzed using an Immunospot Analyzer and Immunospot software package (Cellular Technology, Cleveland, Ohio).

CFSE-Based Proliferation Assay

Purified B cells were resuspended at 1×10$^6$ cells/ml in pre-warmed PBS/0.1% BSA and labeled with carboxyfluorescein diacetate succinimidyl ester (CFSE; Invitrogen) at a final concentration of 0.4 μM for 10 minutes at 37° C. The cells were then washed four times with IMDM containing 5% FCS. CFSE-labeled cells were stimulated with LPS (30 μg/ml) in the presence or absence of sCD40L (100 ng/ml) as described above. After three days, the cells were harvested and CFSE fluorescence intensity was analyzed using a FACsCalibur (BD Biosciences) and WinMDI software (The Scripps Research Institute, San Diego, Calif.). The proliferative index was calculated by dividing the total number of cells in all generations by the calculated number of original parent cells.

Intracellular IgM Staining

Purified B cells were stimulated with LPS in the presence or absence of sCD40L, as described above. Cultures were harvested after three days and stained for intracellular IgM by blocking surface IgM with unlabeled anti-μ (20 μg/ml, clone B7.6) in PBS/2% BSA. The cells were subsequently washed and fixed with 1% paraformaldehyde (Electron Microscopy Services, Hatfield, Pa.) for 10 minutes at 4° C. Fixed cells were permeablized by incubation in PBS/0.5% BSA/0.05% saponin (Sigma) for 30 minutes at 4° C., followed staining with Cy5.5-labeled anti-IgM. The cells were washed and analyzed using a FACsCalibur and WinMDI software.

Example 10

Results

Figure 11:
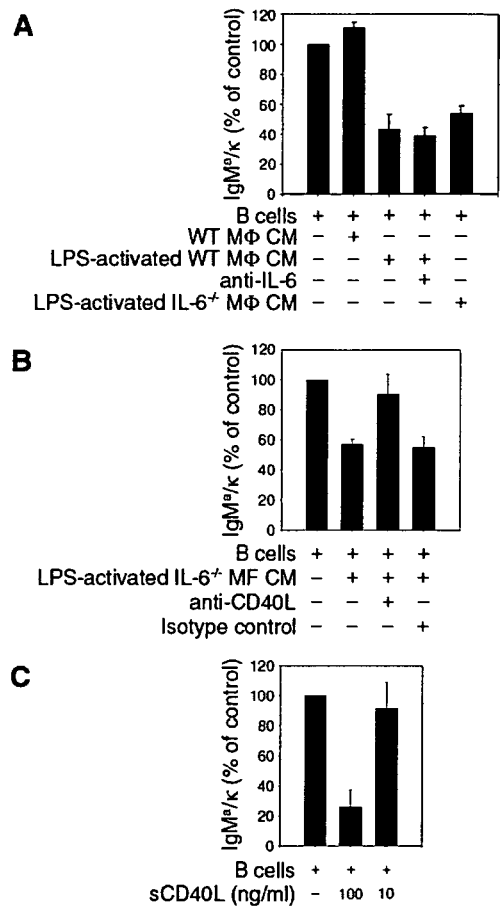
FIG. 11 shows that sCD40L secreted by MΦ represses Ig secretion by Sm-specific B cells. Sm-specific B cells (1×10$^5$) were stimulated with LPS (30 μg/ml) alone or in the presence of either WT MΦ CM, LPS-activated WT MΦ CM, LPS-activated IL-6$^{-/-}$ MΦ CM or anti-IL-6 (50 μg/ml) (A), LPS-activated IL-6$^{-/-}$ CM, anti-CD40L, or isotype-matched control mAb (10 μg/ml) (B), or the indicated concentration of rsCD40L (C). IgM$^a$/κ levels were quantitated on day 4 by ELISA. LPS-stimulated B cells (100%) secreted 1.3-8.5 μg/ml. Data represent at least 3 experiments.

Secretion of CD40 Ligand and IL-6 by MΦs Represses Ig Secretion by Autoreactive B Cells B cells that express the 2-12H immunoglobulin (Ig) transgene paired with a Vk8 Ig light chain transgene bind the small nuclear ribonucleoprotein, Smith (Sm), with low affinity (Retter et al., (1995) *J. Immunol.* 155:2248-2257). Sm-specific B cells from the 2-12H/Vk8 Ig transgenic mice fail to secrete Ig upon stimulation with LPS unless the splenic B cells are purified from DCs and MΦs (Borrero et al., (2002) *J. Immunol.* 168:13-21; Kilmon et al., (2005) *J. Immunol.* 175: 3741). We previously showed that TLR activation of autoreactive B cells was regulated IL-6 secreted by activated DCs (Kilmon et al., (2005) *J. Immunol.* 175:37-41; Examples 5 and 7). Further, like dendritic cells, splenic MΦ and bone marrow-derived MΦ (BMMΦ) repressed LPS-induced Ig secretion by autoreactive B cells (FIG. 20 and Kilmon et al., (2005) *J. Immunol.* 175:37-41). To investigate the mechanisms underlying MΦ-mediated repression, conditioned medium (CM) was prepared from LPS-stimulated BMMΦ to assess if soluble mediators acted on autoreactive B cells to regulate Ig secretion. As shown in FIG. 11 (panel A), CM from unstimulated BMMΦ does not affect Ig secretion by LPS-activated Sm-specific B cells. In contrast, CM prepared from LPS-activated BMMΦ repressed 57% of Ig secretion. BMMΦ secrete significant amounts of IL-6 upon LPS stimulation (36.1±6.8 ng/ml); however anti-IL-6 failed to neutralize the repressive effect. To confirm this finding, LPS-activated BMMΦ CM were prepared from IL-6 deficient (IL-$6^{-/-}$) mice. Similar to the findings that anti-IL-6 failed to neutralize repression, CM prepared from IL-$6^{-/-}$ BMMΦ repressed 47% of Ig secretion. This suggests that despite the presence of IL-6 in the CM, MΦ secrete additional factors that repress Ig secretion by B cells from 2-12H/Vk8 mice.

Figure 12:
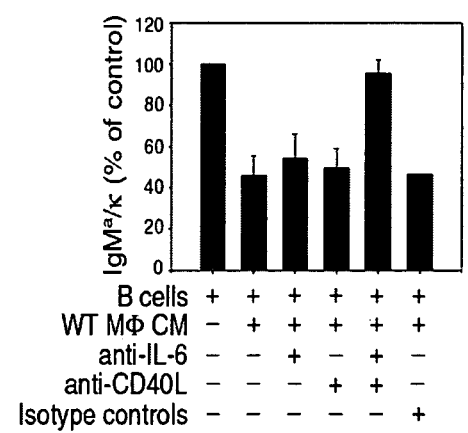
FIG. 12 demonstrates that MΦ secrete at least two soluble factors, IL-6 and sCD40L, that repress Ig secretion by Sm-specific B cells. Sm-specific B cells (1×10$^5$) were stimulated with LPS (30 μg/ml) alone or in the presence of either LPS-activated WT MΦ CM, anti-IL6 (50 μg/ml), anti-CD40L (10 μg/ml) or isotype-matched controls. IgM$^a$/κ levels were quantitated on day 4 by ELISA. LPS-stimulated B cells (100%) secreted 1-3 μg/ml. Data represent 3 experiments.

To identify the other factor(s), the CM from IL-$6^{-/-}$ BMMΦ was neutralized with a panel of antibodies. Neutralization with anti-CD40L relieved the repressive effect seen with the LPS-activated BMMΦ CM (FIG. 11, panel B) restoring Ig levels to 90% of control. To confirm that soluble CD40L repressed Ig secretion, recombinant sCD40L was added to Sm-specific B cell cultures. As shown in FIG. 11 (panel C), recombinant sCD40L inhibited 74% of Ig secretion. To determine if MΦ secreted repressive factors other than IL-6 and sCD40L, LPS-activated BMMΦ CM was neutralized with both anti-IL-6 and anti-CD40L. As shown in FIG. 12, neutralization with either anti-IL-6 or anti-CD40L failed to restore Ig secretion. However, neutralization with both antibodies restored 95% of secretion. Collectively, these data indicate that MΦ repress autoantibody secretion through the production of IL-6 and sCD40L.

Both DCs and MΦ repress Ig secretion by secreting multiple factors suggesting that these cell types play a specialized role in repressing B cell subsets. To examine this possibility, the effects of sCD40L on follicular and marginal zone B cells were compared. Since the 2-12/Vκ8 mice lack marginal zone B cells (Borrero and Clarke (2002) *J. Immunol.* 168:13), follicular and marginal zone B cells were sorted from 2-12H mice. These mice express the same heavy chain as the 2-12/Vκ8 mice and in the absence of the transgenic light chain, the heavy chain pairs with endogenous light chains resulting in receptor/Ag interactions of varying affinities (Santulli-Marotto et al., (1998) *Immunity* 8:209-219). The spleens of these mice are comprised of approximately 60% follicular and 19% marginal zone B cells and about 30% of the B cells bind recombinant Sm. Differentiation of Sm-specific follicular B cells into antibody secreting cells was significantly reduced by addition of DCs, MΦ, IL-6 and sCD40L to the cultures (data not shown). In contrast, Sm-specific marginal zone B cell differentiation was unaffected by DCs and IL-6; however, addition of MΦ or sCD40L reduced differentiation by 57% and 41%, respectively indicating that B cell subsets are differentially regulated by IL-6 and sCD40L.

Figure 13:
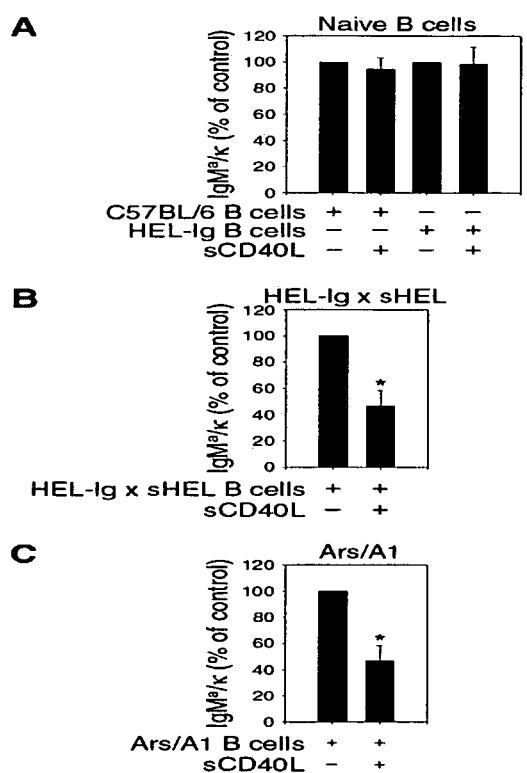
FIG. 13 demonstrates that sCD40L selectively represses chronically Ag-experienced B cells. B cells (1×10$^5$) from C57BL/6 and HEL-Ig (A), HEL-Ig×sHEL (B), or Ars/A1 mice (C) were stimulated with LPS (30 μg/ml) alone or in the presence of sCD40L (10 ng/ml) for 4 days. IgM$^b$ (C57BL/6), anti-HEL IgM$^a$, and IgM$^a$/κ (Ars/A1) were quantitated by ELISA.

It has previously been reported that chronic exposure to autoantigens reprograms the IL-6R on autoreactive B cells such that exposure to IL-6 represses LPS-induced Ig secretion (Kilmon et al., (2005) *J. Immunol.* 175:37-41). To determine if sCD40L exhibited the same selective specificity for repressing autoreactive B cells, the effects of sCD40L on naïve and chronically antigen-experienced B cells were compared. Ig secretion by LPS-stimulated C57BL/6 B cells was similar in the presence or absence of sCD40L (FIG. 13, panel A). Similarly, LPS-induced Ig secretion by naïve HEL-specific B cells (HEL-Ig) was unchanged by the addition of sCD40L. In contrast, anti-HEL secreted by purified HEL-specific B cells chronically exposed to sHEL (HEL-Ig× sHEL) was reduced 53% by the addition of sCD40L (FIG. 13, panel B). To assess if other chronically antigen-experienced B cells were repressed by sCD40L, Ig secretion was measured from B cells specific for the hapten p-azophenylarsonate (Ars). Ars/A1 Ig transgenic mice express a heavy and light chain pair that binds Ars; however, B cells from these mice cross react with ssDNA conferring an anergic phenotype (Benschop et al., (2001) *Immunity* 14:3343; Gauld et al., (2005) *Nat. Immunol.* 6:1160-1167). Similar to the effects on HEL-Ig×sHEL B cells, sCD40 repressed 40% of LPS-induced Ig secretion by purified Ars-specific B cells (FIG. 13, panel C). These data indicate that during innate immune responses, MΦ regulate autoreactive B cells through the secretion of sCD40L.

T cell-dependent signals direct the fate of B cells by regulating proliferation, germinal center formation, class switch recombination, somatic mutation, and memory cell formation. The ability of CD40L to regulate Ig secretion by autoreactive B cells suggested that impaired cell cycle arrest might prevent differentiation of autoreactive B cells. To assess differences in proliferation following CD40 stimulation, naïve (C57BL/6) and autoreactive (2-12H/Vk8) B cells were labeled with CFSE and the number of cells in each division were measured, and the proliferative index (PI) calculated, which is an indication of average number of cells divisions that each cell in culture has undergone (data not shown). Proliferation of LPS-stimulated C57BL/6 B cells was increased when sCD40L was present (PI=5.3 versus 6.6). Proliferation of 2-12H/Vk8 B cells was also increased in the presence of sCD40L (PI=3.7 compared to 5.1); however, the change in proliferation due to sCD40L was comparable between B cells from C57BL/6 and 2-12H/Vk8 mice indicating that 2-12/Vk8 and C57BL/6 B cells proliferate equally in response to sCD40L. Similarly, C57BL/6 and 2-12H/Vk8 B cell cultures yielded similar increases in the number of viable cells after three days in culture with sCD40L (data not shown). This indicates that CD40L-induced repression of Ig secretion is not the result of prolonged proliferation and failure to exit the cell cycle.

To assess if CD40L blocked terminal differentiation similar to the scenario identified in cell fate decisions within the germinal center, intracellular IgM and was quantitated and plasma cell formation enumerated. It was found that 7% of 2-12H/Vk8 B cells became intracellular IgM$^{hi}$ after three days of LPS-stimulation (data not shown). Addition of sCD40L reduced the number of intracellular IgM$^{hi}$ cells by 50%. Paralleling this decrease, the presence of sCD40L in the cultures inhibited the number of ASC by 49% (data not shown). In contrast, the number of intracellular IgM$^{hi}$ cells, and the number of ASCs in LPS-stimulated C57BL/6 cultures was minimally affected by sCD40L treatment (data not shown). These data indicate that CD40L prevents Ig secretion by inhibiting differentiation of autoreactive B cells into plasma cells.

Terminal differentiation of B cells in to plasma cells requires the transcription factors, BLIMP-1 and XBP-1. To elucidate the molecular basis of the block in differentiation caused by sCD40L, BLIMP-1 and XBP-1 mRNA levels were measured by real-time PCR. BLIMP-1 and XBP-1 mRNA in Sm-specific B cells was significantly upregulated by LPS stimulation (data not shown). In contrast, sCD40L treatment reduced BLIMP-1 and XBP-1 mRNA levels by 47% and 58%, respectively, consistent with the observation that sCD40L reduces plasma cell differentiation. These data indicate that sCD40L inhibits plasma cell differentiation upstream of BLMP-1 expression.

Figure 14:
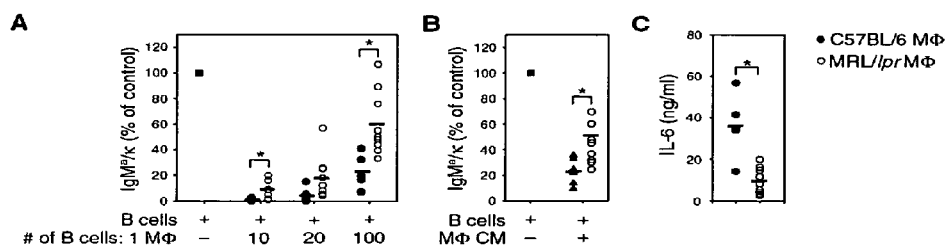
FIG. 14 shows that repression of Ig secretion by MRL/lpr MΦ is defective coincident with a failure to secrete soluble mediators. Sm-specific B cells (1×10$^5$) were stimulated with LPS (30 μg/ml) and cocultured with the indicated number of C57BL/6 or MRL/lpr MΦ (A) or LPS-activated CM from C57BL/6 or MRL/lpr MΦ (B) for 4 days. IgM$^a$/κ was determined by ELISA. C, IL-6 levels in LPS-activated CM from C57BL/6 or MRL/lpr MΦ was determined by ELISA. The horizontal bars mark the mean secretion. (*p≤0.05).

MRL/lpr mice develop an autoimmune disease reminiscent of human systemic lupus erythematosus (SLE). The defects underlying murine or human autoimmune disease are poorly defined. The studies described herein define a novel mechanism of tolerance wherein MΦ repress Ig secretion through the secretion of IL-6 and sCD40L. To test the idea that MΦ-mediated tolerance is defective in lupus-prone mice, the ability of C57BL/6 and MRL/lpr-derived MΦ to repress Ig secretion by B cells from 2-12H/Vκ8 mice was compared. As shown in FIG. 14 (panel A), MΦ from C57BL/6 mice repressed 98% of Ig secretion when co-cultured at a ratio of 20:1 (20 B cells to 1 MΦ), while MΦ from MRL/lpr mice repressed 87% of secretion. At a ratio of 100:1, B6 MΦ repressed 77% while MRL/lpr MΦ repressed 40% of Ig secretion. Similarly, LPS-stimulated CM from MRL/lpr MΦ inhibited Ig secretion less effectively than CM from C57BL/6 mice (FIG. 14, panel B). To determine if the inability of MRL/lpr MΦ to repress Ig secretion correlated with their ability to secrete repressive mediators, the amounts of IL-6 and sCD40L produced from LPS-activated B6 and MRL/lpr MΦ were quantitated. As shown in FIG. 14 (panel C), the amount of IL-6 produced by the MΦ from MRL/lpr mice was significantly reduced compared to the MΦ from C57BL/6 controls. These data indicate that the inability of MΦ from MRL/lpr mice to repress Ig secretion is coincident with their failure to secrete IL-6 and sCD40L.

Example 11

Materials and Methods

DC from Lupus-Prone Mice are Defective in Repressing Ig Secretion

Mice 2-12H/Vκ8/Cκ$^{-/-}$ immunoglobulin transgenic mice were generated as previously described (Borrero et al., (2002) *J. Immunol.* 168:13-21; (Kilmon et al., (2005) *J. Immunol.* 175: 3741). Animals were used at 9-17 weeks of age. MRL/MpJ-Fas$^{lpr}$/J (MRL/lpr) and C57BL/6J (B6) were purchased from The Jackson Laboratory. B6 and MRL/lpr age-matched females were used at 6-10 weeks old. Animals were maintained in an accredited animal facility.

Reagents and Antibodies

Antibodies to CD11c, CD11b, B220, IL-6, and rIL-6 were purchased from BD Biosciences. Antibodies to GR1 and TLR4 were obtained from eBiosciences, phospho-IκBα from Cell Signaling, IκBα and β tubulin from Santa Cruz, and IgG HRP from Promega. Streptavidin-AP was purchased from Southern Biotech, TEPC 183 and *Escherichia coli* 055:B5 LPS from Sigma Aldrich, *E. coli* 0111:B4 LPS from List Biological Laboratories, mouse GM-CSF and IL-4 from PeproTech, poly (I:C) and R848 from InvivoGen, and CpG oligodeoxynucleotides (ODN) and non-CpG ODN from Coley Pharmaceutical Group. JA12.5, 187.1, and HB100 were purified from hybridoma culture supernatant.

Cell Purification

B cells were purified from 2-12H/Vκ8/Cκ$^{-/-}$ spleens by negative selection (StemCell Technologies) as previously described (Kilmon et al., (2005) *J. Immunol.* 175:3741). B cells were ~85% pure with ~7% T cells and ~5% DCs/MΦs as determined by flow cytometry. CD11c$^+$ splenocytes were purified from B6 and MRL/lpr spleens by positive selection (Miltenyi Biotec). The CD11c$^+$ population was ~70% pure with 20% lymphocytes and 10% MΦs. Isolation of splenic CD11c$^+$ cells performed with and without collagenase (Roche) treatment yielded a similar distribution of CD11c$^+$/CD11b$^+$ populations and comparable levels of IL-6 secretion (data not shown). The data generated from splenic DC populations was obtained from non-collagenase treated spleens.

Bone Marrow-Derived DC (BMDC) Cultures

Bone marrow was harvested from the femurs and tibias of B6 and MRL/lpr mice. Following red blood cell lysis, cells were cultured for 5 days in media containing GM-CSF (10 ng/ml) and IL-4 (10 ng/ml). Conditioned medium (CM) was made from 1×10$^4$ BMDCs (0.2 ml) cultured for an additional 4 days with or without Sigma LPS (30 μg/ml). When cultured with purified 2-12H/Vκ8 B cells at 25% of final volume, the CM was equivalent to a 40:1 B cell:DC ratio. 5×10$^5$ BMDCs (0.2 ml) were cultured for an additional 4 days with or without poly (I:C) (50 μg/ml), R848 (10 μg/ml), CpG ODN (1 μg/ml), or non-CpG ODN (1 μg/ml). In experiments where RNA was isolated or nuclear and cytoplasmic extracts were prepared, BMDCs were stimulated with *E. coli* 0111:B4 LPS (List Biological Laboratories) that was re-purified (Hirschfeld et al., (2000) *J. Immunol.* 1645:618-622; Manthey et al., (1994) *J. Immunol.* 153:2653-2663) and confirmed to be unable to induce IL-6 secretion by TLR4$^{-/-}$ DCs.

LPS Stimulation

Splenocytes containing 1×10$^5$ B cells, or the equivalent number of purified B cells, were cultured with Sigma LPS (30 μg/ml) for 4 days. BMDCs, CD11c$^+$ splenocytes, or BMDC CM (25% of final volume) were added to B cell cultures on day 0.

ELISA

IgM$^a$/κ (encoded by 2-12H/Vκ8/Cκ$^{-/-}$) was captured with anti-κ (187.1), detected with biotinylated anti-IgM$^a$ (HB100) and Streptavidin-AP as previously described (Borrero and Clarke (2002) *J. Immunol.* 168:13-21). Purified mouse IgM$^a$/κ (TEPC 183) served as the standard control. IgM$^a$/κ levels were plotted as "percent of control" defined by the level of Ig secretion in LPS-stimulated cultures of purified 2-12H/Vκ8/Cκ$^{-/-}$B cells. This defined 100%. To quantitate IL-6 levels, IL-6 was captured with anti-IL-6 monoclonal Ab (clone MP5-20F3), detected with biotinylated anti-IL-6 monoclonal Ab (clone MP5-32C11) and Streptavidin-AP. Recombinant IL-6 served as the standard control. Data were plotted as concentration of IL-6.

Real Time (RT)-PCR

DNA-free RNA was prepared from BMDCs treated with re-purified List LPS (15 μg/ml) by solubilization in Trizol (Invitrogen) and treatment with Turbo DNase (Ambion). Reverse transcription with oligo(dT) primers was performed with Superscript II (Invitrogen). The amount of IL-6 message was determined using the TaqMan Assay-On-Demand primer-probe sets (Applied Biosystems) and the ABI 7000 sequence detection system. IL-6 mRNA transcript levels were independently normalized to the amount of β-glucuronidase (GUS) transcription in each sample according to the following equation: % GUS=2^[-(GUS-IL-6 units)]. Normalized data were plotted as the log of % GUS.

Electrophoretic Mobility Shift Assay (EMSA)

BMDCs were stimulated with re-purified List LPS (15 μg/ml), nuclear and cytoplasmic extracts were obtained, and gel shift assays were performed as previously described (Mayo et al., (1997) *Science* 278:1812-1815). Briefly, an oligonucleotide corresponding to an NF-κB site from the H-2Kb gene was radiolabeled using [α-32P]dCTP (Perkin Elmer). Probe was incubated with 4 μg of nuclear extract and 0.1 μg/μl poly dIdC in DNA binding buffer (50 mM NaCl, 10 mM Tris pH 7.6, 10% glycerol, 1 mM DTT, 0.5 mM EDTA) for 15 minutes at room temperature. Reactions were separated using non-denaturing PAGE and visualized by autoradiography. For antibody supershift analysis, extracts were preincubated 15 minutes at room temperature with 1 μg of antiserum before the addition of the radiolabeled gel shift probe.

Immunoblot

BMDCs ($2 \times 10^6$) were stimulated with re-purified List LPS (15 μg/ml) and solublized in lysis buffer containing 1% NP40, 150 mM NaCl, 10 mM Tris (pH 7.5), 2 mM sodium o-vanadate, 1 mM PMSF, 0.4 mM EDTA, 10 mM NaF, and 1 μg/ml each of aprotinin, leupeptin, and α1-anti-trypsin. Detergent insoluble material was removed by centrifugation at 12,000×g for 10 minutes. Proteins were resolved by SDS-PAGE and transferred onto PVDF membrane. Phospho-IκBα, IκBα, and β tubulin were immunoblotted with HRP tagged antibodies and detected by enhanced chemiluminescence (ECL, Amersham Biosciences).

Statistical Analysis

Statistical analysis was done using the Student's t test. p values <0.05 were considered significant and denoted by*.

Example 12

Results

DC from Lupus-Prone Mice are Defective in Repressing Ig Secretion

The Frequencies of Splenic myDCs and MΦ are not Diminished in MRL/lpr Mice.

During activation of the innate immune system, maintaining B cell tolerance is crucial in preventing autoimmunity. We have previously shown that stimulation through TLR4 activates myDCs and MΦs to secrete soluble factors, thereby repressing Ig secretion by chronically antigen-experienced (autoreactive) B cells (Kilmon et al., (2005) *J. Immunol.* 175:3741). To determine if the breakdown of tolerance in lupus-prone mice was associated with the lack of a repressive cell type, the frequency of splenic MΦs and DC subsets in MRL/lpr and B6 mice were compared. The frequencies of myDCs ($CD11c^{hi}/CD11b^{int/hi}$) and plasmacytoid DCs (pDCs, $CD11c^{lo}/CD11b^-/B220^+/GR1^+$) were not significantly different (data not shown). The MΦ population ($CD11c^-/CD11b^{hi}$) was increased, but overall this difference did not reach statistical significance. The lymphoid DCs (ly-DCs, $CD11c^{lo}/CD11b^-/B220^-/GR1^-$) were significantly decreased, however this population is not involved in DC/MΦ-mediated tolerance (Kilmon et al., (2005) *J. Immunol.* 175:3741). An increased $CD11c^-/CD11b^{lo}$ population was apparent in the autoimmune MRL/lpr mice; however, this population did not diminish IL-6 production by B6 DCs, or affect the ability of B6 DCs to regulate Ig secretion by Sm-specific B cells (data not shown). Thus, diminished frequency of the repressive myDC and MΦ cell types does not account for the loss of tolerance in MRL/lpr mice.

DCs from MRL/lpr Mice Fail to Efficiently Repress Sm-Specific B Cells.

Figure 15:
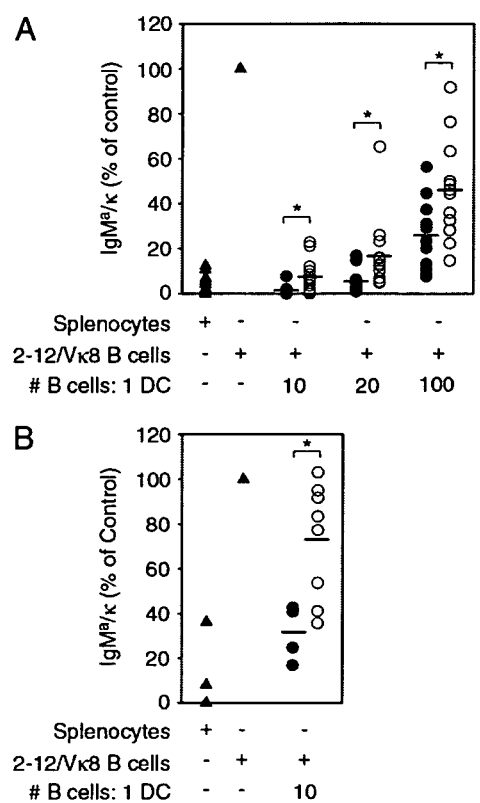
FIG. 15 shows that DCs from MRL/lpr mice fail to efficiently repress Sm-specific Ig secretion. LPS-stimulated (30 μg/ml) splenocytes (1×10$^5$ B cells) or purified B cells (1×10$^5$) were cocultured with the indicated ratios of BMDCs (A), or ex vivo splenic DCs (B). Secreted IgM$^a$/κ levels were quantitated by ELISA from the day 4 culture supernatant. LPS-stimulated purified B cells (100%) secreted 1-10 μg/ml IgM$^a$/κ. Data represent 14 (A) and 8 (B) MRL/lpr mice. (▲Controls, ●B6, ○MRL/lpr) *Denotes statistical significance.

LPS-activated DCs from B6 mice regulate chronically antigen-experienced B cells (Kilmon et al., (2005) *J. Immunol.* 175:3741). To assess if DCs from MRL/lpr mice were capable of repressing Ig secretion, splenic Sm-specific B cells from 2-12H/Vκ8 mice were cocultured with bone marrow-derived DCs (BMDCs) from B6 or MRL/lpr mice (FIG. 15, panel A). Compared to B6 DCs, MRL/lpr DCs were less efficient at repressing Sm-specific B cells when cultured at B cell: DC ratios of 10:1, 20:1, and 100:1 (p=0.018, 0.032, and 0.015 respectively). These differences were not due to contaminating cells, because DCs from both B6 and MRL/lpr mice contained 70-79% myDCs, with the remaining cells being MΦs ($CD11c^-/CD11b^{hi}$). To determine if splenic DCs reflected these same defects, $CD11c^+$ cells were isolated from the spleens of B6 and MRL/lpr mice, and cocultured with B cells from 2-12H/Vκ8 mice (B cell:DC ratio 10:1). As shown in FIG. 15 (panel B), ex vivo B6 DCs repressed significantly better than DCs purified from MRL/lpr mice (p=0.014). Collectively, these data indicate that DCs from MRL/lpr mice are present at a normal frequency, but are defective in their ability to repress Ig secretion by autoreactive B cells.

DCs from MRL/lpr Mice are Defective in IL-6 Secretion

Figure 16:
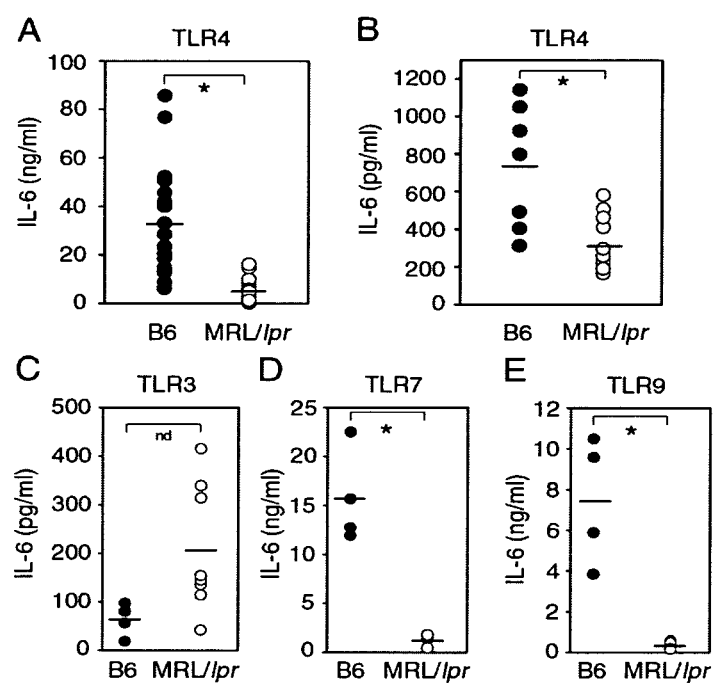
FIG. 16 demonstrates that DCs from MRL/lpr mice are defective in IL-6 secretion. 1×10$^4$ BMDCs (A), or 1×10$^5$ ex vivo splenic DCs (B), were stimulated with LPS (30 μg/ml). 1×10$^5$ BMDCs were stimulated with poly (I:C) (50 μg/ml) (C), R848 (10 μg/ml) (D), and CpG ODN (1 μg/ml) (E). IL-6 was quantitated by ELISA from the day 4 culture supernatants. Data represent 26 (A), 13 (B), 8 (C), 5 (D), and 7 (E) MRL/lpr mice. (▲Controls, ●B6, ○MRL/lpr) *Denotes statistical significance. $^{nd}$Not significantly different.

We previously showed that DC secretion of IL-6 repressed autoreactive B cells (Kilmon et al., (2005) *J. Immunol.* 175: 37-41; Examples 5 and 7). To determine if diminished IL-6 was associated with the inability of MRL/lpr DCs to repress Sm-specific Ig secretion, IL-6 was measured by ELISA. LPS-activated BMDCs (FIG. 16, panel A) and splenic $CD11c^+$ cells (FIG. 16, panel B) from MRL/lpr mice secreted significantly less IL-6 compared to B6 controls (p<0.0001 and p=0.0007 respectively). Diminished IL-6 was not due to a general TLR4 defect because LPS-induced secretion of TGF-β, was comparable in B6 and MRL/lpr mice (data not shown). To determine whether defective IL-6 secretion was limited to TLR4 stimulation, IL-6 secretion was assessed in response to other TLR ligands. As shown in FIG. 16 (panels C-E), IL-6 secretion was defective when MRL/lpr BMDCs were stimulated through TLR7 (R848) and TLR9 (CpG ODN), but not through TLR3 (poly (I:C)) (p=0.0003, 0.0001, and 0.060 respectively). These data indicate that DCs from MRL/lpr mice are defective in IL-6 secretion upon stimulation of the innate immune system. Further, since IL-6 secretion upon TLR3 stimulation was not diminished, mutation within the IL-6 structural gene is unlikely.

Diminished IL-6 Secretion is not Due to Decreased TLR4 Expression.

Expression of TLRs ensures that DCs are activated during innate immune responses. It was possible that the decreased secretion of IL-6 from MRL/lpr DCs reflected a reduced expression of surface TLR4. The expression of TLR4 on myDCs from B6 (MFI 58.9±12.6) and MRL/lpr (MFI 68.1±10.9) mice were not significantly different (data not shown). Likewise, BMDCs from B6 and MRL/lpr mice did not differ in TLR4 expression (data not shown). Thus, diminished surface expression of TLR4 does not account for the decreased IL-6 secretion by LPS-activated DCs from MRL/lpr mice.

Defective IL-6 Secretion is Associated with Failure to Sustain IL-6 Transcription.

Transcriptional regulation of IL-6 depends on several signal transduction pathways that activate NF-κB. To determine if the diminished secretion of IL-6 by MRL/lpr DCs was due to defective transcriptional regulation, BMDCs from B6 and MRL/lpr mice were LPS-stimulated and IL-6 mRNA levels measured by real time-PCR. Basal levels of IL-6 mRNA were not different between the B6 and MRL/lpr mice (data not shown). Six hours after LPS stimulation, half of the MRL/lpr mice showed a significant induction in IL-6 mRNA levels, comparable to B6 mice. Despite an initial induction of IL-6 transcription, all of the MRL/lpr mice failed to sustain elevated IL-6 message levels when compared to B6 mice. These data show that DCs derived from MRL/lpr mice fail to sustain IL-6 mRNA levels coincident with diminished IL-6 secretion.

Regulation of the IL-6 gene occurs through several cis-acting elements, including the transcription factor NF-κB (Dendorfer et al., (1994) *Mol. Cell. Biol.* 14:4443-4454). To assess if decreased IL-6 mRNA levels were associated with defects in nuclear translocation of NF-κB, the DNA binding activity of nuclear extracts prepared from B6 and MRL/lpr DCs were compared. B6 DCs showed DNA binding of NF-κB within 45 minutes of LPS stimulation, with robust binding at six hours. In contrast, DCs from MRL/lpr mice showed diminished basal and LPS-induced NF-κB DNA binding at the same timepoints (data not shown). To identify the NF-κB subunits involved in DNA binding, the DNA/protein complex was supershifted with subunit-specific antibodies. p65 and c-Rel were identified as components of the NF-κB complex formed in B6 DCs following LPS stimulation (data not shown).

Nuclear translocation of NF-κB is dependent on phosphorylation and degradation of IκB (Karin, (1999) *Oncogene* 18:6867-6874; Israel, (2000) *Trends Cell Biol.* 10:129-133; Htada et al., (2000) *Curr. Opin. Immunol.* 12:52-58). To assess if the failure to translocate NF-κB was associated with defects in IκB phosphorylation, whole cell lysates from LPS-stimulated B6 and MRL/lpr BMDCs were immunoblotted. B6 DCs showed induced phosphorylation of IκBα at 5 minutes, with a low level of sustained phosphorylation at 6 hours (data not shown). In contrast, MRL/lpr DCs induced comparable IκBα phosphorylation at 5 minutes, but failed to sustain phosphorylation at later timepoints (data not shown). Collectively, these data indicate that the initial phosphorylation of IκBα in MRL/lpr and B6 DCs produced comparable IL-6 mRNA levels at 6 hours; however, the failure to sustain IκB phosphorylation and NF-κB activation may attenuate IL-6 transcription and protein synthesis in MRL/lpr DCs. These data show that continuous TLR4 signal transduction is required to maintain IL-6 secretion.

Autoantibody Secretion is Repressed by IL-6 and Another Soluble Factor(s).

Figure 17:
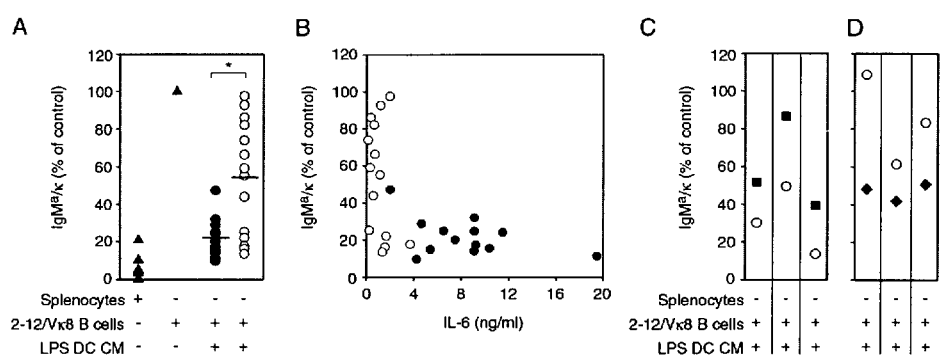
FIG. 17 shows that, in addition to IL-6, other soluble factors regulate autoantibody secretion. Purified B cells from 2-12H/Vκ8 mice were stimulated with LPS (30 μg/ml) in the absence (▲) or presence of DC CM from B6 mice (●) or MRL/lpr mice (○) (A). The repressive ability of IL-6 in DC CM (25% of final volume, equivalent to B cell:DC ratio of 40:1) from B6 (●) and MRL/lpr (○) was plotted relative to IgM$^a$/κ secretion by B cells from 2-12H/Vκ8 mice (1×10$^5$) (B). DC CM from individual MRL/lpr mice was untreated (○) or neutralized with anti-IL-6 antibody (50 μg/ml) (■) prior to coculture with B cells from 2-12H/Vκ8 mice. Each column represents the DC CM from individual MRL/lpr mice (C).

We have previously shown that IL-6 repressed 75% of Ig secretion by Sm-specific B cells (Kilmon et al., (2005) *J. Immunol.* 175:3741; Examples 5 and 7). It is shown here that decreased IL-6 levels correlate with an autoimmune phenotype. To determine the importance of decreased IL-6 in the breakdown of tolerance, the ability of conditioned medium (CM) from B6 and MRL/lpr DCs to repress Ig secretion was assessed. CM allowed us to distinguish the effects of soluble mediators from the effects of cell contact. As shown in FIG. 17 (panel A), DC CM from most B6 mice repressed 70-90% of Ig secretion. In contrast, the repressive ability of DC CM from MRL/lpr mice was extremely variable (10-90% repression). This broad range of repression did not always correlate with IL-6 levels. As shown in FIG. 17 (panel B), despite the low levels of IL-6 exhibited by all MRL/lpr mice, some still repressed 80-90% of Ig secretion. To assess if the low levels of IL-6 contributed to Ig repression, any remaining IL-6 in the DC CM was neutralized. Neutralization of IL-6 in MRL/lpr CM from three individual mice partially relieved repression, confirming that IL-6 contributed to the repression of Ig secretion (FIG. 17, panel C). However, full secretion (100%) was never attained, suggesting that in addition to IL-6, other DC-derived soluble mediators regulate Ig secretion. It was possible that the variability in repression was due to the secretion of an activating factor by the DCs from MRL/lpr mice. To address this, recombinant IL-6 (rIL-6) to the MRL/lpr DC CM were added, and then Ig secretion by Sm-specific B cells was assessed. When added to the CM from three individual mice, rIL-6 repressed Ig secretion indicating that if activating factors were present, they did not override the repressive effect of rIL-6 (FIG. 17, panel D). In addition, MRL/lpr DC CM did not increase secretion by Sm-specific B cells in the absence of LPS (data not shown), suggesting that an activator was not likely to be responsible for the increased Ig in these cultures. These data show that despite impaired IL-6 production, the DCs from some MRL/lpr mice regulate autoreactive B cells by secreting other soluble mediators.

Example 13

Effect of Self-Antigen on Tolerizing Auto-Reactive B Cells

During autoimmunity, the tolerance mechanisms that regulate autoreactive B cells become dysregulated. Our studies assessing the regulation of TLR-induced Ig secretion identified that DCs and MΦs regulated LPS-induced Ig. We have shown that IL-6 secreted from DCs and MΦ repressed B cells that had been chronically exposed to self-antigen. These findings implicate a role for self-antigen; however its role in regulating innate and antigen-induced Ig secretion remains unclear. To define the role of self-antigen in tolerance to Smith (Sm), an immunoglobulin transgenic model expressing the 2-12H heavy chain paired with the Vκ8 light chain was used. Smith antigen, an integral component of the snRNP complex, is immunogenic in SLE. It has previously been shown that Sm is contained within the cytoplasm and the nucleus in a relatively diffuse staining pattern. In addition, Sm translocates to the plasma membrane during apoptosis. Thus, the valency of Sm varies suggesting that the form of the tolerizing antigen might affect the state of unresponsiveness.

It was hypothesized that different forms of self-antigen regulate autoreactive B cells to different extents. To test this hypothesis, autoreactive B cells from several immunoglobulin transgenic models that bind self-antigen with varying affinity/avidity were evaluated. B cells specific for hen egg lysozyme (HEL) showed that splenic B cells (splenocytes) chronically exposed to soluble HEL failed to secrete Ig upon LPS exposure (FIG. 19, left panel). However, removal of self-antigen and other splenic populations through negative selection dramatically increased the ability of these cells to secrete Ig. In contrast, coculture of purified HEL-specific B cells with soluble HEL completely repressed Ig secretion, suggesting that soluble HEL alone is sufficient to repress Ig secretion. In contrast, analysis of autoreactive B cells specific for ssDNA and the hapten, p-azophenylarsonate (Ars) showed that although Ars$_7$BSA completely repressed LPS-induced Ig secretion, although ssDNA only partially repressed secretion (FIG. 19, right panel). This indicates that different forms of self-antigen affect the degree of B cell unresponsiveness. To identify if Sm played a role in the regulation of Ig secretion, and to identify the nature of the self-antigen involved in unresponsiveness to Sm, Sm-specific B cells were cocultured with purified, soluble Sm, snRNP complexes, and soluble Sm immobilized to plastic. As shown in FIG. 18, LPS-induced Ig secretion was unaffected by the presence of soluble Sm or by the snRNP complex, but Sm immobilized to plastic efficiently repressed Ig secretion. This suggests that only high valency immobilized antigen regulate the secretion of Sm-specific autoantibody during innate immune responses.

Dendritic cells and MΦ function in the clearance of apoptotic cells through multiple receptors including Mer, Tyro3 and Axel, CD36, $\alpha_v\beta_5$ integrin, scavenger receptors and phosphatidylserine receptor. In addition, antibody-coated cells and complement-coated cells associate with surface Fc and complement receptors, raising the possibility that apoptotic antigens are displayed on the surface of DCs and MΦs. In support of this, others have reported that immune complexes are recycled and displayed on the surface of DCs to activate B cells and that loading exogenous hen egg lysozyme leads to B cell interactions with dendritic cells. To investigate the possibility that nuclear-antigens were displayed on the surface of DCs and MΦ, bone marrow derived DCs (BMDC), bone marrow-derived MΦ (BMMΦ), and CD11c$^+$ splenic cells were stained for Sm. BMDCs BMMΦ and ex vivo CD11c$^+$ cells showed staining with anti-Sm (data not shown). Further, trypsin removed the anti-Sm stain indicating that a surface protein was binding the anti-Sm antibody. To confirm that the anti-Sm antibody recognized Smith antigen, the antibody was adsorbed with recombinant SmD, then stained BMDCs. Cells stained with antibody adsorbed with BSA remained surface Sm positive, while cells stained with antibody adsorbed with recombinant SmD failed to show the presence of Sm (data not shown). These data indicate that the anti-Sm antibody specifically stained Sm protein.

Previously, others had reported that in addition to Sm, histone and DNA were present on the surface of apoptotic cells. If the source of the Sm on DCs and MΦ was apoptotic cells, it was reasoned that other nuclear antigens might also be present. To investigate this possibility, BMDCs and BMMΦs were stained with antibodies specific for histone and dsDNA. BMDCs and BMMΦs showed the presence of histones and dsDNA (data not shown). Further, treatment of cells with DNase removed the antigen recognized by the anti-DNA, indicating that the antigen was localized on the cell surface.

The observations that nuclear self-antigens were displayed by DCs and MΦ raised the possibility that all self-antigens were on the surface of DCs and MΦs. To investigate this, CD11c$^+$ splenic DC/MΦ population from mice expressing a hen egg lysozyme transgene (ML5) were stained. These mice constitutively secrete soluble HEL with serum levels approximating 15 ng/ml. Under these conditions, soluble HEL induces a state of unresponsiveness in B cells expressing HEL-specific BCR. Exogenous HEL (500 ng) bound to the HEL-specific BCR of the D1.3 cell line showed the presence of HEL indicating that the anti-HEL antibody was capable of detecting surface HEL (data not shown). In contrast, CD11c$^+$ splenocytes stained under the same conditions failed to show the presence of HEL. To eliminate the possibility that lymphocytes displayed nuclear self-antigen, splenic B and T cells were sorted and stained for Sm. The presence of CD3 and B220 identified the T and B cell populations; however, neither population displayed surface Sm, restricting the presence of these antigen to the DC/MΦ population. Together these data indicate that only splenic DCs and MΦ display nuclear antigens on their cell surfaces.

Example 14

DCs and MΦ Repress Ig Secretion by Sm-Specific B Cells

B cells from mice expressing the 2-12H Ig heavy chain transgene (IgM$^a$) paired with a Vκ8 light chain transgene bind Sm with low affinity and are tolerized by peripheral anergy (Borrero et al., (2002) *J. Immunol.* 168:13-21). During the characterization of anergic, Sm-specific B cells, it was unexpectedly observed that purified B cells secreted IgM$^a$/κ in response to LPS, whereas unpurified splenocytes remained LPS-unresponsive (FIG. 20, panel A). Interestingly, reconstitution of purified Sm-specific B cells with B cell-depleted splenocytes (henceforth called non-B cells) repressed IgM$^a$/κ secretion. Non-B cells from non-Tg mice also inhibited secretion, indicating that repression was not specific to 2-12H/Vκ8 mice (FIG. 20, panel A). These data show that the unresponsive phenotype of Sm-specific B cells is reversible and conferred by non-B cells.

To identify the regulatory cell(s) that repressed Ig secretion, ex vivo DCs, MΦ, T cells, NK cells, and NK T cells were co-cultured with purified Sm-specific B cells. T cells, NK cells, and NK T cells failed to inhibit LPS-induced-IgM$^a$/κ secretion (FIG. 20, panel B). However, ex vivo DCs (CD11c$^+$) and MΦ (CD11b$^+$) repressed 75% of secretion when one DC or MΦ was co-cultured with ten B cells (FIG. 20, panel B). To confirm that MΦ and DCs repressed Ig secretion, bone marrow-derived MΦ (BMMΦ) and DCs (BMDCs) were co-cultured with Sm-specific B cells at increasing B:DC ratios. BMMΦ and BMDCs repressed approximately 95% of IgM$^a$/κ secretion when cultured at a ratio of 10:1 (ten B cells to one BMMΦ or BMDC) (FIG. 20, panel C). At 100:1, BMMΦ repressed 85% of IgM$^a$/κ, while BMDCs repressed only 38%. These data indicate that DCs and MΦ maintain autoreactive B cells in an unresponsive state, but that BMMΦ are more potent repressors than BMDCs.

To identify the subsets of CD11c$^+$/CD11b$^+$ cells responsible for DC/MΦ-mediated repression, MΦ, myDCs, lyDCs, and pDCs were purified from non-Tg mice and co-cultured with Sm-specific B cells (FIG. 21, panel A). As shown in FIG. 21 (panel B), both lyDCs and pDCs failed to repress Ig secretion. In contrast, myDCs repressed 48% and MΦ repressed 83% of LPS-induced IgM$^a$/κ secretion when cultured at a ratio of 10:1 (ten B cells to one myDC or MΦ. At a ratio of 20:1, splenic myDCs repressed only 29% of secretion, while splenic MΦ repressed 70%. These data identify myDCs and MΦ as regulatory cells that repress LPS-induced Ig secretion and corroborate the findings that splenic MΦ and BMMΦ are more efficient at repressing Ig secretion than splenic DCs and BMDCs.

The foregoing is illustrative of the present invention, and is not to be construed as limiting thereof. The invention is defined by the following claims, with equivalents of the claims to be included therein.

The invention claimed is:

1. A method of repressing B cell autoantibody secretion in a mammalian subject diagnosed with an autoimmune disorder, the method comprising:
  administering a plurality of allogeneic hematopoietic stem cells (HSC) that can differentiate into dendritic cells and/or macrophages to the mammalian subject in an amount effective to repress B cell autoantibody secretion in the mammalian subject, and
  administering to the mammalian subject an agent that activates dendritic cells and/or macrophages through a Toll Like receptor (TLR), CD40 antigen and/or a TNF receptor to secrete a soluble factor that represses B cell autoantibody secretion.

2. The method of claim 1, wherein the plurality of HSC are isolated HSC.

3. The method of claim 1, wherein the mammalian subject is given a bone marrow transplant, wherein the bone marrow transplant comprises the plurality of HSC.

4. The method of claim 1, wherein the soluble factor comprises a cytokine.

5. The method of claim 1, wherein the soluble factor comprises IL-6, TNF-α, CD40 ligand, or a combination thereof.

6. The method of claim 1, wherein the autoreactive B cell is a plasma cell, plasmablast, marginal zone cell, B1 cell, transitional B cell and/or follicular B cell.

7. A method of treating an autoimmune disorder in a mammalian subject diagnosed with an autoimmune disorder, the method comprising:
    administering allogeneic hematopoietic stem cells (HSC) that can differentiate into dendritic cells and/or macrophages to the mammalian subject in an amount effective to treat the autoimmune disorder, and
    administering to the mammalian subject an agent that activates dendritic cells and/or macrophages through a Toll Like receptor (TLR), CD40 antigen and/or a TNF receptor to secrete a soluble factor that represses B cell autoantibody secretion.

8. The method of claim 7, wherein the method further comprises administering to the mammalian subject a treatment-effective amount of a B cell depletion therapy.

9. The method of claim 7, wherein the B cell depletion therapy is administered prior to administration of the HSC.

10. The method of claim 7, wherein the plurality of HSC are isolated HSC.

11. The method of claim 7, wherein the mammalian subject is given a bone marrow transplant, wherein the bone marrow transplant comprises the plurality of HSC.

12. The method of claim 7, wherein the soluble factor comprises a cytokine.

13. The method of claim 7, wherein the soluble factor comprises IL-6, TNF-α, CD40 ligand, or a combination thereof.

14. The method of claim 1, wherein the mammalian subject is a human subject.

15. The method of claim 7, wherein the mammalian subject is a human subject.

16. A method of repressing B cell autoantibody secretion in a mammalian subject diagnosed with systemic lupus erythematosis, the method comprising:
    administering a plurality of allogeneic hematopoietic stem cells (HSC) that can differentiate into dendritic cells and/or macrophages to the mammalian subject in an amount effective to repress B cell autoantibody secretion in the mammalian subject.

17. The method of claim 16, wherein the plurality of HSC are isolated HSC.

18. The method of claim 16, wherein the mammalian subject is given a bone marrow transplant, wherein the bone marrow transplant comprises the plurality of HSC.

19. The method of claim 16, wherein the mammalian subject is a human subject.

20. A method of treating systemic lupus erythematosis (SLE) in a mammalian subject diagnosed with SLE, the method comprising:
    administering allogeneic hematopoietic stem cells (HSC) that can differentiate into dendritic cells and/or macrophages to the mammalian subject in an amount effective to treat SLE.

21. The method of claim 20, wherein the method further comprises administering to the mammalian subject a treatment-effective amount of a B cell depletion therapy.

22. The method of claim 21, wherein the B cell depletion therapy is administered prior to administration of the HSC.

23. The method of claim 20, wherein the plurality of HSC are isolated HSC.

24. The method of claim 20, wherein the mammalian subject is given a bone marrow transplant, wherein the bone marrow transplant comprises the plurality of ENC.

25. The method of claim 20, wherein the mammalian subject is a human subject.

* * * * *

UNITED STATES PATENT AND TRADEMARK OFFICE
CERTIFICATE OF CORRECTION

PATENT NO. : 8,795,653 B2  
APPLICATION NO. : 11/376375  
DATED : August 5, 2014  
INVENTOR(S) : Vilen et al.

Page 1 of 1

It is certified that error appears in the above-identified patent and that said Letters Patent is hereby corrected as shown below:

In the Specification:
Column 27, Line 31: correct "14:3343)" to read -- 14:33-43) --
Column 34, Line 5: correct "14:3343)." to read -- 14:33-43). --
Column 35, Line 24: correct "14:3343)." to read -- 14:33-43). --
Column 37, Line 16: correct "3741)." to read -- 37-41). --
Column 38, Line 30: correct "14:3343;" to read -- 14:33-43; --
Column 39, Line 60: correct "3741)." to read -- 37-41). --
Column 40, Line 14: correct "175:3741)." to read -- 175:37-41). --
Column 41, Line 56: correct "175:3741)." to read -- 175:37-41). --
Column 42, Line 1: correct "175:3741)." to read -- 175:37-41). --
Column 42, Line 12: correct "175:3741)." to read -- 175:37-41). --
Column 43, Line 57: correct "175:3741;" to read -- 175:37-41; --
Column 45, Line 48: correct "MΦ" to read -- MΦs --
Column 45, Line 66: correct "MΦ" to read -- MΦs --

In the Claims:
Column 48, Line 39, Claim 24: correct "plurality of ENC."
to read -- plurality of HSC. --

Signed and Sealed this
Third Day of February, 2015

Michelle K. Lee
*Deputy Director of the United States Patent and Trademark Office*